US008920851B2

(12) United States Patent
Hovens et al.

(10) Patent No.: US 8,920,851 B2
(45) Date of Patent: Dec. 30, 2014

(54) TREATMENT OF NEURODEGENERATIVE DISEASES

(75) Inventors: Christopher Hovens, Surrey Hills (AU); Niall Corcoran, Flemington (AU)

(73) Assignee: Velacor Therapeutics Pty Ltd, Parkville (AU)

( * ) Notice: Subject to any disclaimer, the term of this patent is extended or adjusted under 35 U.S.C. 154(b) by 519 days.

(21) Appl. No.: 12/295,270

(22) PCT Filed: Mar. 29, 2007

(86) PCT No.: PCT/AU2007/000391
§ 371 (c)(1),
(2), (4) Date: Jan. 16, 2009

(87) PCT Pub. No.: WO2007/109851
PCT Pub. Date: Oct. 4, 2007

(65) Prior Publication Data
US 2009/0169649 A1    Jul. 2, 2009

Related U.S. Application Data

(60) Provisional application No. 60/787,240, filed on Mar. 29, 2006.

(51) Int. Cl.
*A61K 33/04* (2006.01)
*A61K 45/06* (2006.01)

(52) U.S. Cl.
CPC ............... *A61K 33/04* (2013.01); *A61K 45/06* (2013.01)
USPC .......................................................... 424/702

(58) Field of Classification Search
None
See application file for complete search history.

(56) References Cited

U.S. PATENT DOCUMENTS

| | | | | |
|---|---|---|---|---|
| 4,810,497 | A * | 3/1989 | Horrobin ...................... | 424/677 |
| 5,925,349 | A | 7/1999 | Rosen et al. | |
| 6,746,678 | B1 * | 6/2004 | Shapiro ........................ | 424/400 |
| 2002/0061870 | A1 | 5/2002 | Pearson et al. | |
| 2003/0175361 | A1 * | 9/2003 | Vaddadi ........................ | 424/702 |
| 2004/0076758 | A1 | 4/2004 | Lettmann et al. | |
| 2005/0142216 | A1 | 6/2005 | Rindlesbach | |
| 2007/0026090 | A1 * | 2/2007 | Tirosh et al. .................. | 424/702 |
| 2008/0004255 | A1 | 1/2008 | Lyons et al. | |

FOREIGN PATENT DOCUMENTS

| | | |
|---|---|---|
| AU | 2005/227420 A1 | 5/2007 |
| EP | 234733 B1 | 11/1991 |
| EP | 1774972 A1 | 4/2007 |
| JP | 62185018 A | 8/1987 |
| JP | 04-247033 | 9/1992 |
| JP | H10-500939 | 1/1998 |
| JP | 2005-525329 A | 8/2005 |
| JP | 2007106732 A | 4/2007 |
| JP | 2009532340 | 9/2009 |
| WO | 9524920 | 9/1995 |
| WO | WO 03/066071 A1 | 8/2003 |
| WO | 2004016597 A2 | 2/2004 |
| WO | WO 2007/109851 A1 | 10/2004 |
| WO | 2004099168 A2 | 11/2004 |
| WO | WO 2005017143 A1 | 2/2005 |
| WO | WO 2005/023274 A1 | 3/2005 |
| WO | WO 2007/109853 A1 | 10/2007 |

OTHER PUBLICATIONS

Mayo clinic alzheimers; [online] retrieved from http://www.mayoclinic.com/health/alzheimers-disease/DS00161/METHOD=print on Jan. 29, 2011; 12 pages.*
Mayo clinic parkinsons disease; [online] retrieved from http://www.mayoclinic.com/health/parkinsons-disease/DS00295 on Jan. 29, 2011; 9 pages.*
Zwillich "Panel: No Evidence of Alzheimer's Prevention" [online] retrieved from http://www.webmd.com/alzheimers/news/20100428/panel-no-evidence-alzheimers-prevention on Jan. 29, 2011; Apr. 28, 2010; 2 pages.*
Corcoran et al. (Journal of Clinical Neuroscience 2010, 17, pp. 1025-1033).*
Alzheimer's [online] retrieved on May 5, 2013 from: http://www.mayoclinic.com/health/alzheimers-disease/DS00161; Jan. 19, 2013; 15 pages.*
Dementia [online] retrieved on May 5, 2013 from: http://www.mayoclinic.com/health/dementia/DS01131; Apr. 16, 2013; 17 pages.*
Alzheimer's [online] retrieved on May 5, 2013 from: http://www.cdc.gov/features/alzheimers/; Jun. 4, 2010; 5 pages.*
What Causes Parkinson's Disease? [online] retrieved on May 6, 2013 from: http://www.webmd.com/parkinsons-disease/guide/parkinsons-causes; Aug. 13, 2012; 3 pages.*
Foster et al. (Ann Neurol 1997; 41:706-715).*
Lei et al. (The International Journal of Biochemistry & Cell Biology 2010, 42, 1775-1778).*
Ehmann et al. (Abstract of: Ann Neurol. 1984. 15(1):102-4) 1 page.*
Bouma, et al., Cerebral circulation and metabolism after severe traumatic brain injury: the elusive role of ischemia, J. Neurosurg, 1991, vol. 75, pp. 685-693.
Cho, et al., Brain Slices as Models for Neurodegenerative Disease and Screening Platforms to Identify Novel Therapeutics, Discovery Neuroscience, Wyeth Research, 2007, vol. 5, pp. 19-33, Princeton, USA.
Davis, et al., The chemical forms of selenium influences 3,2'-Dimethyl-4-aminobiphenyl-DNA adduct formation in Rat colon, Biochemical and Molecular Roles of Nutrients, 1999, pp. 63-69.
Feng, et al., Dietary Selenium Reduces the Formation of Aberrant Crypts in Rats Administered 3,2' - Dimethyl-4-aminobiphenyl, Toxicology and Applied Pharmacology, 1999, vol. 157, pp. 36-42.

(Continued)

*Primary Examiner* — Ernst V Arnold
(74) *Attorney, Agent, or Firm* — Knobbe, Martens, Olson & Bear, LLP

(57) ABSTRACT

The present invention relates to the use of selenate or a pharmaceutically acceptable salt thereof in methods and compositions for enhancing the activity of the protein phosphatase PP2A. Methods of reducing phosphorylation of tau protein, inhibiting activity of GSK3 and treating or preventing neurodegenerative diseases are also described.

9 Claims, 17 Drawing Sheets

(56) References Cited

OTHER PUBLICATIONS

Finley, et al., Selenium (Se) from high-selenium broccoli is utilized differently than selenite, selenate and selenomethionine, but is more effective in inhibiting colon carcinogenesis, BioFactors, 2001, vol. 14, pp. 191-196.

Klevay, Pharmacology and toxicology of heavy metals: Selenium, (Pharmacology & Therapeutics. Part A: Chemotherapy, Toxicology and Metabolic Inhibitors), 1976, vol. 1(2), pp. 211-222.

Lu et al., Dissociation of the Genotoxic and Growth Inhibitory Effects of Selenium, Biochemical Pharmacology, 1995, vol. 50, Issue 2, pp. 213-219.

Mayo Clinic, Huntington's Disease, [online] retrieved from http://www.mayoclinic.com/health/huntingtons-disease/DS00401/METHOD=print (cited in the Office Action dated Feb. 3, 2011 in U.S. Appl. No. 12/681,569), May 8, 2009, pp. 8 pages.

Mayo Clinic, Anxiety, [online] retrieved from http://www.mayoclinic.com/health/anxiety/DS01187/METHOD=print (cited in the Office Action dated Feb. 3, 2011 in U.S. Appl. No. 12/681,569), Jun. 29, 2010, pp. 9 pages.

Mayo Clinic, Creutzfeldt-jakob, [online] retrieved from http://www.mayoclinic.com/health/depression/DS00175/METHOD=print (cited in the Office Action dated Feb. 3, 2011 in U.S. Appl. No. 12/681,569), May 14, 2010, pp. 7.

Mayo Clinic, Depression [online] retrieved from http://www.mayoclinic.com/health/depression/DS00175/METHOD=print (cited in the Office Action dated Feb. 3, 2011 in U.S. Appl. No. 12/681,569) Feb. 11, 2010, 14 pages.

Mayo Clinic, Epilepsy, [online] retrieved from http://www.mayoclinic.com/health/epilepsy/DS00342/METHOD=print (cited in the Office Action dated Feb. 3, 2011 in U.S. Appl. No. 12/681,569), Apr. 28, 2009, pp. 10.

Mayo Clinic, Schizophreniaalzheimers, [online] retrieved from http://www.mayoclinic.com/health/schizophrenia/DS00196/METHOD=print (cited in the Office Action dated Feb. 3, 2011 in U.S. Appl. No. 12/681,569), Jan. 30, 2010, pp. 8 pages.

Menter, et al., Selenium Effects on Prostate Cell Growth, Cancer Epidemiol Biomarkers & Prevention, 2000, vol. 9, pp. 1171-1182.

Ramaekers, et al., Selenium deficiency triggering intractable seizures, Neuropediatric, 1994, vol. 25(4), pp. 217-223.

Stewart, et al., Selenium Compounds Have Disparate Abilities to Impose Oxidative Stress and Induce Apoptosis, Free Radical Biology & Medicine, 1999, vol. 26, pp. 42-48.

Van Eersel, et al, Sodium selenate mitigates tau pathology, neurodegeneration, and functional deficits in Alzheimer's disease models, Proc. Nat'l. Acad. Sci. USA, 2010, vol. 107, Issue 31, pp. 13888-13893.

Weber, et al., Glutathione peroxidase deficiency and childhood seizures, Lancet, 1991, Issue 337, pp. 1443-1444.

Kasuya, "Effect of Selenium on the Toxicity of Methylmercury on Nervous Tissue in Culture", Toxicology and Applied Pharmacology, 1976, 35, pp. 11-20.

Zafar, et al., "Dose-dependent protective effect of selenium in rat model of Parkinson's disease: neurobehavioral and neurochemical evidences", Journal of Neurochemistry, 2003, 84, pp. 438-446.

Vaddadi, et al., "Low blood selenium concentrations in schizophrenic patients on clozapine", 2003 Blackwell Publishing Ltd. Br J Clin Pharmacol. 55, pp. 307-309.

Vinson, et al., "Comparison of the Toxicity of Inorganic and Natural Selenium", Selenium in Biology and Medicine, edited by Combs, G.F., Levander, O.A., Spallholz, J.E. and Oldfield, J.E. Van Nostrand, NY., 1987, in 2 pages.

Sajatovic, et al., "Clozapine therapy in patients with neurological illness," Int. J. Psychiatry Med. 25:331 (1995).

Calomme et al. (Selenium Deficiency Triggering Intractable Seizures in Therapeutic Uses of Trace elements 1996 Springer NY pp. 359-364).

Calbom (The Juice Lady's Guide to Juicing for Health, 1999, Penguin p. 150).

Schweizer et al. "Selenium and brain function: a poorly recognized liaison", Brain Research Reviews 2004 (45) 164-178.

Oztas, et al. "Influence of Antioxidants on the Blood-Brain Barrier Permeability During Epileptic Seizures" Journal of Neuroscience Research, 2001, vol. 66, pp. 674-678.

Gupta, et al. "Neuroprotective effect of antioxidants on ischaemia and reperfusion-induced cerebral injury", Pharmacological Research, 2003, vol. 43, pp. 209-215.

Santamaria et al, "Protective effects of the antioxidant selenium on quinolinic acid-induced neurotoxicity in rats: in vitro and in vivo studies", Journal of Neurochemistry, 2003, vol. 86, pp. 479-488.

Kern et al, "Massive cerebral embolization: successful treatment with retrograde perfusion", Ann Thorac Surg 2000, 69: pp. 1266-1268.

Delacourte, "Tauopathies: recent insights into old diseases", Folia Neuropathologica, 2005, 43(4):244-257.

Mayo clinic alzheimer's; [online] retrieved from http://www.mayoclinic.com/health/alzheimers-disease/DS00161/METHOD=print on Jan. 29, 2011; 12 pages.

Mayo clinic alzheimer's; [online] retrieved from http://ww.mayoclinic/health/parkinsons-disease/DS00295 on Jan. 29, 2011; 9 pages.

Alzheimer's disease, Mayoclinic [online] retrieved from: http://www.mayoclinic.org/diseases-conditions/alzheimers-disease/basics/definition/con-20023871; Jan. 19, 2013; 15 pages.

Belikov, Pharmaceutical Chemistry, M. Higher School, 1993, pp. 43-46.

Always, et al. "Stroke Essentials for Primary Care: A Practical Guide 2009", 3 pages.

* cited by examiner

A

B

C

D

A

B

C

A

B

A

B

A

B

A

B

A

B ern Phase of International
TREATMENT OF NEURODEGENERATIVE DISEASES

This application is U.S. National Phase of International Application PCT/AU2007/000391, filed Mar. 29, 2007 designating the U.S., and published in English as WO 2007/109851 on Oct. 4, 2007, which claims priority to U.S. Provisional Application No. 60/787,240 filed Mar. 29, 2006.

FIELD OF THE INVENTION

This invention relates to the use of selenate or a pharmaceutically acceptable salt thereof in methods and compositions for enhancing the activity of PP2A. The present invention also relates to the use of selenate or a pharmaceutically acceptable salt thereof in methods of inhibiting or reducing phosphorylation of tau protein, in methods of inhibiting the activity of GSK3β and particularly in methods of treating or preventing neurodegenerative diseases. In some embodiments, the invention relates to the use of selenate or a pharmaceutically acceptable salt thereof in combination with other therapies for use in methods of treating or preventing neurodegenerative diseases.

BACKGROUND OF THE INVENTION

Neurodegenerative disease is a general term for a number of disorders that act by compromising the brain's capacity to control itself or the body by damaging neurons that facilitate normal brain function. Neurodegenerative diseases are primarily diseases of older people. With an increase in life expectancy, the world's population is living longer and the number of sufferers of neurodegenerative diseases has been increasing.

In a number of neurodegenerative disorders, there is a deposition of abnormal tau protein in neurons and glial cells in the brain. For example, abnormal tau protein has been found in neurofibrillary tangles characteristic of Alzheimer's disease (AD). Neurofibrillary tangles (NTs) are one of the two neuropathological hallmarks of AD [Lee et al., 2001]. Paired helical filaments (PHFs) are the major structural component of NTs and are mainly composed of microtubule-associated protein tau [Lee et al., 1991, Grundke-Iqbal et al. 1986a, Grundke-Iqbal et al., 1986b]. PHF-tau (tau protein isolated from PHFs) is highly insoluble, displays retarded mobility on SDS gel and is incapable of binding to microtubules because it is abnormally phosphorylated (phosphorylated on more sites than in normal tau protein) [Lee et al., 1991, Grundke-Iqbal et al. 1986a, Grundke-Iqbal et al., 1986b]. Upon dephosphorylation, PHF-tau becomes soluble and as capable as normal tau protein in binding and promoting microtubule assembly [Wang et al., 1995,Wang et al., 1996, Bramblett et al., 1993]. Abnormal tau phosphorylation is believed to cause tau dysfunction, microtubule instability, axonal transport loss, neurodegeneration and dementia associated with AD [Alonso et al., 1996].

One type of abnormal tau protein is hyperphosphorylated tau protein. Tau protein is known to be phosphorylated at a number of phosphorylation sites by glycogen synthase kinase 3β (GSK3β) in vivo, including the Alzheimer's disease specific Ser$^{396}$ residue [Li and Paudel, 2006]. In turn, GSK3β is known to be phosphorylated by the protein kinase Akt and the activity of Akt is known to be attenuated by the protein phosphatase PP2A.

PP2A is a heterotrimeric holoenzyme that exists in multiple forms composed of a common core structure bound to different regulatory subunits [Mumby and Walter, 1993]. The core enzyme is a complex between the catalytic (C) and structural (A) subunits. A third class of subunit, termed B, comprises several polypeptides that regulate PP2A activity and specificity [Mumby and Walter, 1993, Kamibayashi et al. 1994]. A significant portion of the ABC isoform of PP2A is associated with neuronal microtubules [Sontag et al., 1995], implicating PP2A in the regulation of the phosphorylation state of microtubule-associated proteins (MAPs), such as tau. PP2A containing the B regulatory subunits, but not other forms of PP2A, (i.e. B' and B") has been shown to bind and potently de-phosphorylate tau in vitro. Furthermore, inhibiting the ABC isoform of PP2A induces hyperphosphorylation of tau, dissociation of tau from microtubules and loss of tau-induced microtubule stabilisation [Sontag et al., 1996]. It has recently been shown that PP2A accounts for approximately 71% of the total tau phosphatase activity of human brain [Liu et al., 2005]. The total phosphatase activity and the activities of PP2A toward tau are significantly decreased in brains of AD patients whereas that of other phosphatases such as PP2B are actually increased in the AD brain [Liu et al., 2005]. PP2A activity negatively correlates to the level of tau phosphorylation at most phosphorylation sites in human brains. This indicates that PP2A is the major tau phosphatase that regulates its phosphorylation at multiple sites in human brain. This implies that the abnormal hyperphosphorylation of tau is partially due to a downregulation of PP2A activity in AD brain and that agents that can act to boost the activity of PP2A and in particular the ABC isoform of PP2A would have clinical utility in treating and or preventing development of neurodegenerative diseases.

There is also increasing evidence that abnormal phosphorylation of tau protein may be associated with neurodegenerative disorders in which abnormal α-synuclein protein is present. Tau and α-synuclein pathology both occur in Alzheimer's disease, Parkinson's disease, Guam-Parkinson-ALS-dementia complex and Parkinson's disease caused by mutations in α-synuclein (Duda et al., 2002, Forman et al., 2002, Ishizawa et al., 2003).

The protein α-synuclein appears to play an important role in the pathophysiology of Parkinson's disease (PD). Lewy bodies are a pathological hallmark of PD that are composed primarily of α-synuclein (Spillantini et al., 1997; Spillantini et al., 1998b).

α-Synuclein is thought to play a critical role in the pathophysiology of PD because it accumulates in Lewy bodies and because genetic studies identified mutations in α-synuclein that are associated with familial PD (Kruger et al., 1998; Polymeropoulos et al., 1997; Singleton et al., 2003; Spillantini et al., 1998b; Zarranz et al., 2004).

The A53T and A30P mutations in α-synuclein appear to be causative in PD by increasing the tendency of α-synuclein to aggregate. The mutations both increase the tendency of α-synuclein to aggregate spontaneously or in response to exogenous factors, such as metals and oxidative stress (Conway et al., 2000; Hashimoto et al., 1999; Kruger et al., 1998; Ostrerova-Golts et al., 2000; Paik et al., 1999, 2000; Polymeropoulos et al., 1997).

The A53T and A30P mutations in α-synuclein also cause age-dependent α-synuclein aggregation and neuronal injury in transgenic mice and Drosophila (Feany and Bender, 2000; Giasson et al., 2002; Kahle et al., 2001; Masliah et al., 2000). These results emphasize the relevance of α-synuclein to the study of neurodegeneration.

Abnormal phosphorylated tau is present in Lewy bodies found in sporadic PD patients and occurs in neurons near areas containing α-synuclein pathology (Ishizawa et al., 2003). In vitro evidence also links α-synuclein and tau as α-synuclein binds tau in vitro, and stimulates tau phosphorylation by protein kinase A in vitro (Giasson et al., 2003; Jensen et al., 1999). Recent results indicate that α-synuclein enhances tau fibrillization in vitro and that abnormal tau fibrils are present in the brains of symptomatic transgenic mice overexpressing mutant A53T α-synuclein (Giasson et al., 2003).

Frasier M et al. 2005 have shown that A30P α-synuclein aggregation occurs alongside tau pathology and that α-synuclein aggregation occurs in parallel with tau pathology in transgenic mice overexpressing A30P α-synuclein, and have shown that symptomatic A30P α-synuclein transgenic mice exhibit abnormal tau phosphorylation and that the phosphorylation correlates with activation of a c-jun kinase.

Apart from aggregation of α-synuclein (α-Syn), oxidative stress and exposure to certain neurotoxins such as 1-methyl-4-phenyl-1,2,3,6-tetrahydropyridine (MPTP) are linked to the pathogenesis of PD. MPTP induces a selective degeneration of the nigrostriatal dopaminergic pathway in mice and primates, as seen in PD, associated with increases in α-Syn expression levels and aggregation, but without inducing real Lewy bodies (Dauer and Przedborski, 2003), but triggering formation of nigral inclusions immunoreactive for ubiquitin and α-synuclein on continuous administration of MPTP (Fornai et al., 2005). Another component of certain Lewy bodies is abnormally phosphorylated tau (Ishizawa et al., 2003). Neuronal colocalization of tau and α-Syn as aggregates or inclusions, or inside certain Lewy bodies or Lewy body-like inclusions, has been reported in brains of patients with familial Alzheimer's disease (AD), Down's syndrome, and Lewy body disease (Kotzbauer et al., 2001; Lippa et al., 1999; Arima et al., 1999; Iseki et al., 1999).

Similarities between tau and α-Syn include expression in presynaptic neurons, long half-lives in vivo, their "natively unfolded" nature allowing for their heat stability, and their propensity to fibrillize through stretches of hydrophobic residues that form the core of assembled fibrils (Friedhoff et al., 2000; Serpell et al., 2000).

Other in vitro data with the [396/404]S 3E double mutant (a pseudophosphorylation construct mimicking the PHF-1 phosphorylation sites in which the two serine residues at position 396 and 404 in the longest human isoform of tau, ht40, were replaced into glutamate residues) tau also indicate that hyperphosphorylation at Ser396/404 may cause the C terminus of tau to assume a more extended conformation, altering its inhibitory effect on tau oligomerization and potentiating the rate of filament formation (Abraha et al., 2000).

Duka T et al., 2006, have now shown that MPTP-induced increases in α-Syn expression levels in mesencephalic dopaminergic neurons promote changes in the phosphorylation patterns of tau at the PHF-1 binding site (Ser396/404), resulting in a mislocation of both proteins and with increased coimmunoprecipitation, together with increased levels of sarkosyl-insoluble hyperphosphorylated tau, suggesting that an initial step in MPTP-induced parkinsonism and neurotoxicity, is α-Syn-directed hyperphosphorylaton of Tau at Ser396/404.

The findings that MPTP causes increased dissociation of α-Syn from microtubules, together with decreases in phosphorylated-tau levels associated with the cytoskeletal bound fraction, may also be of relevance to the mechanism(s) underlying the neurodegenerative process. Hyperphosphorylation of tau greatly reduces the affinity of tau for microtubules, causing their destabilization (Drechsel et al., 1992; Biernat et al., 1993; Michaelis et al., 2002). In addition, phosphorylated-tau is also known to bind to and deplete other microtubule binding proteins, such as MAP1 and MAP2, from microtubules (Iqbal and Grundke-Iqbal, 2005). Moreover, since α-Syn is known to bind to microtubules (Wersinger and Sidhu, 2005) with a possible role in axonal transport (Sidhu et al., 2004), it is likely that the dissociation of this protein from microtubules further aggravates the instability of microtubules, disrupting the cytoskeletal network and cellular homeostasis. Thus, the dissociation of α-Syn from microtubules and abnormalities in the properties of tau bound to microtubules, may comprise another link in the chain of events leading to the neurodegenerative processes associated with inclusion formation.

MPTP-induced abnormalities in α-Syn levels modulate phosphorylated-tau formation, and the PHF-1 form of tau, in particular, provide insights in the development of the early phases of both PHF formation and associated loss of vital neuronal function and suggest that MPTP-induced parkinsonian syndromes or neurotoxicity may be a tauopathy with concomitant alterations in α-Syn in a manner reminiscent of synucleopathies.

This suggests that abnormalities of a protein (tau) known to be mobilized during the pathogenesis of AD, may also be mobilized in parkinsonism but in a region of the brain not associated with AD, thereby suggesting considerable overlap in the genesis of certain neurodegenerative diseases. This suggests that neurodegenerative diseases that seem unrelated may actually have common triggering events and subsequent pathologies, which sets in motion neuronal degeneration.

There is a need for agents that affect the phosphorylation of tau protein and are clinically useful in the treatment or prevention of neurodegenerative disorders.

SUMMARY OF THE INVENTION

The present invention is predicated in part on the discovery that the activity of the protein phosphatase PP2A can be enhanced by exposure to selenate or a pharmaceutically acceptable salt thereof. The enhancement of the activity of PP2A can reduce or inhibit phosphorylation of tau protein, especially hyperphosphorylation, with a two pronged approach: i) dephosphorylation and inactivation of Akt, thereby reducing phosphorylation of GSK3β and consequently reducing phosphorylation of tau protein, and ii) direct dephosphorylation of tau protein. A reduction in the phosphorylation, especially hyperphosphorylation of tau protein reduces or prevents the accumulation or deposition of abnormal tau protein in neurons and glial cells and therefore is useful in the treatment or prevention of neurodegenerative disorders.

Accordingly, in one aspect, the present invention provides a method for the treatment or prevention of a neurodegenerative disease in a subject comprising administering to the subject an effective amount of selenate or a pharmaceutically acceptable salt thereof. In some embodiments the neurodegenerative disease is a tauopathy. In some embodiments the neurodegenerative disease is an α-synucleopathy. In specific embodiments, the neurodegenerative disease is selected from presenile dementia, senile dementia, Alzheimer's disease and Parkinson's disease.

In another aspect of the invention there is provided a method of inhibiting or reducing phosphorylation of a tau protein in a neuron, glial cell or Lewy body, comprising exposing the neuron or glial cell to an effective amount of selenate or a pharmaceutically acceptable salt thereof. In some embodiments, the tau protein is a microtubule-associated tau protein. In some embodiments, the tau protein is in a neurofibrillary tangle. In some embodiments, hyperphosphorylation of tau protein is inhibited or prevented.

In yet another aspect, the present invention provides a method of enhancing the activity of PP2A comprising exposing the PP2A to an effective amount of selenate or a pharmaceutically acceptable salt thereof. In some embodiments, the PP2A is an isoform that dephosphorylates Akt. In some embodiments, the PP2A is an isoform that dephosphorylates tau proteins, especially microtubule-associated tau proteins found in neurons and glial cells and Lewy bodies.

In a further aspect, the present invention provides a method of inhibiting the activity of GSK3β in a neuron or glial cell, comprising exposing the neuron or glial cell to an effective amount of selenate or a pharmaceutically acceptable salt thereof.

In a further aspect of the invention, there is provided a use of selenate or a pharmaceutically acceptable salt thereof in the manufacture of a medicament for treating or preventing a neurodegenerative disease.

In some embodiments of the methods and uses broadly described above, the selenate or a pharmaceutically acceptable salt thereof is administered in combination with other therapies suitable for treatment or prevention of neurodegenerative diseases or therapies suitable for relieving the symptoms of neurodegenerative diseases.

DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size or amount that varies by as much as 30%, 20% or 10% to a reference quantity, level, value, dimension, size or amount.

Throughout the specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The term "dephosphorylation" as used herein, refers to the chemical removal of a phosphate group ($PO_4^{2-}$) from a biochemical entity such as a protein. Under cellular conditions, dephosphorylation is achieved enzymatically by an enzyme such as a phosphatase.

As used herein, the terms "glial cell" and "glial cells" refer to non-neuronal cells that provide structural and metabolic support for neurons in the central nervous system. Glial cells may also be referred to as neuroglia or glia.

The term "hyperphosphorylation" refers to the circumstance where all available phosphorylation sites on a biochemical entity such as a protein, are phosphorylated. No further phosphorylation of the biochemical entity can occur. The phrase "inhibiting or reducing hyperphosphorylation" includes preventing all sites on a biochemical entity from being phosphorylated and decreasing the number of biochemical entities that have all of their phosphorylation sites phosphorylated.

As used herein, the term "in combination with" refers to the treatment of a subject with at least two agents such that their effects on the neurodegenerative disease occur, at least in part, over the same time period. Administration of at least two agents may occur simultaneously in a single composition, or each agent may be simultaneously or sequentially administered in separate compositions.

The terms "Lewy body" and "Lewy bodies" refer to abnormal aggregates of protein that develop in nerve cells. The primary protein aggregate in a Lewy body is composed of α-synuclein.

The term "neurodegenerative disease" as used herein, refers to a neurological disease characterised by loss or degeneration of neurons, Neurodegenerative diseases include neurodegenerative movement disorders and neurodegenerative conditions relating to memory loss and/or dementia. Neurodegenerative diseases include tauopathies and α-synucleopathies. Examples of neurodegenerative diseases include, but are not limited to, presenile dementia, senile dementia, Alzheimer's disease, Parkinsonism linked to chromosome 17 (FTDP-17), progressive supranuclear palsy (PSP), Pick's disease, primary progressive aphasia, frontotemporal dementia, corticobasal dementia, Parkinson's disease, Parkinson's disease with dementia, dementia with Lewy bodies, Down's syndrome, multiple system atrophy, amyotrophic lateral sclerosis (ALS) and Hallervorden-Spatz syndrome.

The term "neurofibrillary tangles" as used herein, refers to abnormal structures located in the brain and composed of dense arrays of paired helical filaments (neurofilaments and microtubules). Neurofibrillary tangles include tau proteins, particularly microtubule-associated tau proteins. The number of neurofibrillary tangles present in a brain is believed to correlate with the degree of dementia in the subject. Neurofibrillary tangles are a distinguishing characteristic of Alzheimer's disease.

As used herein, the term "neuron" refers to cells found in the central nervous system that are specialised to receive, process and transmit information. Neurons may also be referred to as nerve cells.

As used herein, the term "nutritional amount" includes an amount of selenium that provides an average daily intake. In the United States, the average daily intake is 80-120 μg/day.

By "pharmaceutically salt" as used herein in relation to selenate, means metal ion salts which are toxicologically safe for human and animal administration. For example, suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, iron, nickel, zinc, ammonium and alkylammonium.

Basic nitrogen-containing groups may be quarternised with such agents as lower alkyl halide, such as methyl, ethyl, propyl and butyl chlorides, bromides and iodides; dialkyl sulfates like dimethyl and diethyl sulfate; and others.

Suitable metal ion salts of selenate include, but are not limited to, sodium, potassium, lithium, magnesium, calcium, iron, nickel, zinc, ammonium and alkylammonium salts. In some embodiments the salt is not lithium selenate. A preferred salt of selenate is the sodium salt, $Na_2SeO_4$.

The term "phosphorylation" as used herein refers to the chemical addition of a phosphate group ($PO_4^{2-}$) to a biochemical entity such as a protein. Under cellular conditions phosphorylation is achieved enzymatically by an enzyme such as a kinase. The phrase "inhibiting or reducing phosphorylation" includes preventing phosphorylation of one or more phosphorylation sites on a biochemical entity, including preventing phosphorylation of all phosphorylation sites as in hyperphosphorylation. This phrase also includes decreasing the extent of phosphorylation of a biochemical entity by preventing phosphorylation occurring at one or more phosphorylation sites or as a result of dephosphorylation occurring at one or more phosphorylated sites on the biochemical entity.

The terms "subject" or "individual" or "patient", used interchangeably herein, refer to any subject, particularly a vertebrate subject and more particularly a mammalian subject, for whom prophylaxis or treatment is desired. Suitable vertebrate animals that fall within the scope of the invention include, but are not limited to, primates, avians, livestock animals (e.g. pigs, sheep, cows, horses, donkeys), laboratory test animals (e.g. rabbits, mice, rats, guinea pigs, hamsters), companion animals (e.g. cats and dogs) and captive wild animals (e.g. foxes, deer, dingoes). A preferred subject is a human in need of treatment or prophylaxis of a neurodegenerative disease, especially Alzheimer's disease or dementia. However, it will be understood that the aforementioned terms do not imply that symptoms are present.

The term "supranutritional" as used herein, refers to an amount which is greater than the amount considered as a nutritional requirement. In the United States, the average daily intake of selenium is 80-120 µg/day. A supranutritional amount of selenium provides selenium to a subject above the recommended daily allowance. For example, a supranutritional amount of selenium may be 3 µg/kg to 20 mg/kg per day, 0.015 mg/kg to 20 mg/kg, 0.1 mg/kg to 20.0 mg/kg, 0.1 mg/kg to 14 mg/kg, 0.1 mg/kg to 13 mg/kg, 0.1 mg/kg to 12 mg/kg, 0.1 mg/kg to 10 mg/kg, 0.1 mg/kg to 9 mg/kg, 0.1 mg/kg to 8 mg/kg, 0.1 mg/kg to 7 mg/kg, 0.1 mg/kg to 6 mg/kg, 0.15 mg/kg to 5 mg/kg, 0.15 mg/kg to 4 mg/kg, 0.15 mg/kg to 3 mg/kg, 0.15 mg/kg to 2 mg/kg, 0.15 mg/kg to 1 mg/kg per day, especially 0.1 mg/kg to 14 mg/kg, 0.07 mg/kg to 6.5 mg/kg or 0.15 mg/kg to 5 mg/kg per day, more especially 0.07 mg/kg to 2 mg/kg per day.

As used herein, the term "α-synucleopathy" refers to a neurodegenerative disorder or disease involving aggregation of α-synuclein or abnormal α-synuclein in nerve cells in the brain. α-Synucleopathies include, but are not limited to, Parkinson's disease, Parkinson's disease with dementia, dementia with Lewy bodies, Pick's disease, Down's syndrome, multiple system atrophy, amylotrophic lateral sclerosis (ALS) and Hallervorden-Spatz syndrome.

As used herein, the term "effective amount" in the context of treating or preventing a neurodegenerative disease or inhibiting or reducing phosphorylation of tau protein or inhibiting the activity of GSK3β is meant the administration or addition of an amount of selenate or a pharmaceutically acceptable salt thereof, either in a single dose or as part of a series of doses, that is effective in enhancing the activity of PP2A and especially that is effective for the prevention of incurring a symptom, holding in check such symptoms, and/or treating existing symptoms, associated with the neurodegenerative disease. The effective amount will vary depending on the health and physical condition of the individual to be treated, the taxonomic group of the individual to be treated, the formulation of the composition, the assessment of the medical situations and other relevant factors. It is expected that the amount will fall within a relatively broad range that can be determined through routine trials. In specific embodiments, a effective amount is a nutritional or supranutritional amount.

The term "tauopathy" as used herein refers to a neurodegenerative disorder or disease involving the deposition of abnormal tau protein isoforms in neurons and glial cells in the brain. Taopathies include diseases and disorders in which tau proteins are abnormally phosphorylated, including tau protein which is hyperphosphorylated. Tauopathies include, but are not limited to, presenile dementia, senile dementia, Alzheimer's disease, Parkinsonism linked to chromosome 17 (FTDP-17), progressive supranuclear palsy (PSP), Pick's disease, primary progessive aphasia, frontotemporal dementia and corticobasal dementia.

2. Methods of Treating or Preventing Neurodegenerative Diseases

The present invention is predicated in part on the determination that selenate or a pharmaceutically acceptable salt thereof, is effective in enhancing the activity of PP2A which in turn may result in a reduction in phosphorylation of tau protein by GSK3β and/or an increase in the rate of dephosphorylation of tau protein. The methods of the invention generally comprise exposing PP2A present in neurons or glial cells to a PP2A activity enhancing amount of selenate or a pharmaceutically acceptable salt thereof. Suitably, the PP2A activity enhancing amount of selenate is a nutritional or supranutritional amount of selenate or a pharmaceutically acceptable salt thereof. In some embodiments, the amount of selenate or a pharmaceutically acceptable salt thereof, especially selenate or a salt thereof, is from about 0.015 mg/kg to about 20 mg/kg, usually from about 0.1 mg/kg to 14 mg/kg, 0.07 mg/kg to 6.5 mg/kg or 0.15 mg/kg to 5 mg/kg per day, for example, 0.07 mg/kg to 2 mg/kg per day.

The present invention can be used effectively to treat or prevent neurodegenerative diseases. Neurodegenerative diseases include neurodegenerative movement disorders and neurodegenerative diseases associated with memory loss and include tauopathies and α-synucleopathies. Illustrative examples of neurodegenerative diseases include presenile dementia, senile dementia, Alzheimer's disease, Parkinsonism linked to chromosome 17 (FTDP-17), progressive supranuclear palsy (PSP), Pick's disease, primary progessive aphasia, frontotemporal dementia, corticobasal dementia, Parkinson's disease, Parkinson's disease with dementia, dementia with Lewy bodies, Down's syndrome, multiple system atrophy, amyotrophic lateral sclerosis (ALS) and Hallervorden-Spatz syndrome. In preferred embodiments, the invention is suitable for treating or preventing tauopathies, especially Alzheimer's disease and dementia. In other embodiments, the invention is suitable for treating or preventing an α-synucleopathy, especially Parkinson's disease. Suitably, the effective amount of selenate or a pharmaceutically acceptable salt thereof is a nutritional or supranutrional amount of selenate. In some embodiments, the amount of selenate or a pharmaceutically acceptable salt thereof, is from about 0.015 mg/kg to about 20 mg/kg, usually from about 0.1 mg/kg to 14 mg/kg or 0.07 mg/kg to 6.5 mg/kg or 0.15 mg/kg to 5 mg/kg per day, for example, 0.07 mg/kg to 2 mg/kg per day. In preferred embodiments, the selenate or a pharmaceutically acceptable salt thereof is sodium selenate ($Na_2SeO_4$).

In some embodiments, the selenate or a pharmaceutically acceptable salt thereof is administered to a subject in combination with another therapy for treating or preventing a neurodegenerative disease. Illustrative examples of therapies for treating or preventing a neurodegenerative disease that may be used in combination with selenate or a pharmaceutically acceptable salt thereof include, but are not limited to, cholinesterase inhibitors such as Tacrine (Cognex®), Donepezil, Galantamine and Rivastigmine; N-methyl-D-aspartate (NMDA) receptor antagonists such as Memantine; estrogen therapies such as Premarin, non-steroidal anti-inflammatory drugs (NSAIDs) such as aspirin and ibuprofen, levodopa (L-Dopa), dopa decarboxylase inhibitors such as Carbidopa and benserazide, or combinations of L-Dopa and a dopa decarboxylase inhibitor, such as sinemet® and Stalevo®, dopamine agonists such as bromocriptine (Parlodel®), pergolide (Permax®), pramipexole (Mirapex®), ropinirole (Requip®), cabergoline, apomorphine (APOKYN™) and lisuride, mono-amine oxidase B inhibitors such as selegiline (Eldepryl® and Carbex®) and rasagiline (Azilect®), anticholinergics such as benzotropine mesylate (Cogentin®) and trihexyphenidyl hydrochloride (Artane®) and COMT inhibitors such as Entacapone (Commtan®) and Tolcapone (Tasmar®), or other medications such as rivastigmine tartrate (Exelon®) and Amantadine (Symmeterl®); or mixtures of two or more of levodopa, dopa decarboxylase inhibitors, dopamine agonists, mono-amine oxidase B inhibitors, anticholinergics or COMT inhibitors.

Combination therapies could include effective amounts of selenate or a pharmaceutically acceptable salt thereof together with an agent used for treating or preventing a neurodegenerative disease in an amount normally used in the absence of selenate. For example, tacrine hydrochloride may be administered as part of a combination with selenate or a pharmaceutically acceptable salt thereof to patients with a neurodegenerative disease such as AD in an amount of 40 mg/day to 160 mg/day or donepezil may be administered in an amount of 5-10 mg/day. Premarin may be administered at a dosage to achieve 1.25 mg/day of conjugated equine estrogens (CEEs) in patients with dementia. Alternatively the amount of agent used in the treatment of neurodegenerative disorders may be decreased upon co-administration with selenate or a pharmaceutically acceptable salt thereof. In some embodiments, the combination may display a synergistic effect.

Certain embodiments of the present invention are directed to methods for treating or preventing neurodegenerative diseases in a subject, which methods generally comprise administering to the subject an effective amount of selenate or a pharmaceutically acceptable salt thereof. To practice these methods, the person managing the subject can determine the effective dosage form of selenate or a pharmaceutically acceptable salt thereof for the particular condition and circumstances of the subject. An effective amount of selenate is one that is effective for the treatment or prevention of a neurodegenerative disease, including prevention of incurring a symptom, holding in check a symptom and treating a symptom. In some embodiments, the effective amount is a nutritional amount. In other embodiments, the effective amount is a supranutritional amount. In specific embodiments, the selenate or a pharmaceutically acceptable salt thereof is sodium selenate.

Modes of administration, amounts of selenate administered, and selenate formulations, for use in the methods of the present invention, are discussed below. The neurodegenerative disease to be treated may be determined by measuring one or more diagnostic parameters indicative of the course of the disease, compared to a suitable control. In the case of a human subject, a "suitable control" may be the individual before treatment, or may be a human (e.g., an age-matched or similar control) treated with a placebo. In accordance with the present invention, the treatment of neurodegenerative diseases includes and encompasses without limitation: (i) preventing a neurodegenerative disease in a subject who may be predisposed to the disease but has not yet been diagnosed with the disease and, accordingly, the treatment constitutes prophylactic treatment for the neurodegenerative disease; (ii) inhibiting a neurodegenerative disease, i.e., arresting the development of the neurodegenerative disease; or (iii) relieving symptoms resulting from the neurodegenerative disease.

The methods of the present invention are suitable for treating an individual who has been diagnosed with a neurodegenerative disease, who is suspected of having a neurodegenerative disease, or who is known to be susceptible and who is considered likely to develop a neurodegenerative disease.

In some embodiments of the above methods, the neurodegenerative disease is a tauopathy, especially Alzheimer's disease or dementia and the treatment optionally further comprises administration of another agent suitable for treating a taupathy as described above.

In other embodiments of the above methods, the neurodegenerative disease is an α-synucleopathy, especially Parkinson's disease and the treatment optionally further comprises administration of another agent suitable for treating an α-synucleopathy as described above.

In preferred embodiments, the selenate is sodium selenate.

Exemplary subjects for treatment with the methods of the invention are vertebrates, especially mammals. In certain embodiments, the subject is selected from the group consisting of humans, sheep, cattle, horses, bovine, pigs, dogs and cats. A preferred subject is a human.

The selenate or a pharmaceutically acceptable salt thereof may be formulated by following any number of techniques known in the art of drug delivery. Selenate or a pharmaceutically acceptable salt thereof may of course be administered by a number of means keeping in mind that all formulations are not suitable for every route of administration. Selenate or a pharmaceutically acceptable salt thereof can be administered in solid or liquid form. The application may be oral, rectal, nasal, topical (including buccal and sublingual), or by inhalation. Selenate or a pharmaceutically acceptable salt thereof may be administered together with conventional pharmaceutical acceptable adjuvant, carriers and/or diluents.

The solid forms of application comprise tablets, capsules, powders, pills, pastilles, suppositories and granular forms of administration. They may also include carriers or additives, such as flavors, dyes, diluents, softeners, binders, preservatives, lasting agents and/or enclosing materials. Liquid forms of administration include solutions, suspensions and emulsions. These may also be offered together with the above-mentioned additives.

Solutions and suspensions of selenate or a pharmaceutically acceptable salt thereof, assuming a suitable viscosity for ease of use, may be injected. Suspensions too viscous for injection may be implanted using devices designed for such purposes, if necessary. Sustained release forms are generally administered via parenteral or enteric means. Parenteral administration is another route of administration of the selenate or a pharmaceutically acceptable salt thereof used to practice the invention. "Parenteral" includes formulations suitable for injection and for nasal, vaginal, rectal, and buccal administration.

The administration of selenate or a pharmaceutically acceptable salt thereof may involve an oral prolonged dose formulation. Oral dose formulations are preferably administered once daily to three times daily in the form of a sustained release capsule or tablet, or alternatively as an aqueous based solution. Selenate or a pharmaceutically acceptable salt thereof may be administered intravenously either daily, continuously, once a week or three times a week.

The administration of selenate or a pharmaceutically acceptable salt thereof may include daily administration, preferably once daily in the form of a sustained release capsule or tablet, or once daily as an aqueous solution.

Combinations of selenate or a pharmaceutically acceptable salt thereof and at least one agent that is suitable for treating a neurodegenerative disease and may be administered in solid or liquid form in a single formulation or composition or in separate formulations or compositions. In some embodiments, the selenate or a pharmaceutically acceptable salt thereof and the agent for treating a neurodegenerative disease are administered orally as a single tablet or capsule or separate tablets or capsules. In other embodiments, the selenate or a pharmaceutically acceptable salt thereof and the agent for treating a neurodegenerative disease are administered intravenously in a single composition or separate compositions.

The present invention also provides pharmaceutical compositions for treating or preventing a neurodegenerative disease, comprising a nutritional or supranutritional amount of selenate or a pharmaceutically acceptable salt thereof. In some embodiments, the compositions contain from about 0.5 mg to about 1.0 g, for example, 5 mg to 450 mg, of selenate or a pharmaceutically acceptable salt thereof, and a pharmaceutically acceptable carrier. In some embodiments, the selenate or its pharmaceutically acceptable salt is in an amount of about 5.0 mg to about 700 mg or 5 mg to 450 mg. In illustrative examples, the selenate or a pharmaceutically acceptable salt thereof is an amount of about 1.6 mg to 450 mg, 5 mg to 450 mg, 7.5 mg to 250 mg, especially 50 mg to 200 mg, for example, 50 mg to 100 mg or 100 mg to 150 mg for a single or divided daily dose. In some embodiments, the pharmaceutical compositions are useful for treating or preventing a taupathy, especially Alzheimer's disease or dementia. In other embodiments, the pharmaceutical compositions are useful for treating or preventing an α-synucleopathy, especially Parkinson's disease.

The pharmaceutical compositions comprising selenate or a pharmaceutically acceptable salt thereof may further comprise another agent for treating or preventing a neurodegenerative disease. For example, the composition may contain selenate or a pharmaceutically acceptable salt thereof and a cholinesterase inhibitor such as Tacrine, Donepezil, Galantamine or Rivastigmine, an N-methyl-D-aspartate (NMDA) receptor antagonist such as Memantine, an estrogenic agent such as Premarin or a non-steroidal anti-inflammatory drug (NSAID) such as aspirin or ibuprofen, levodopa, a dopa decarboxylase inhibitor, combinations of levodopa and a dopa decarboxylase inhibitor and/or a COMT inhibitor, a dopamine agonist, a monoamine oxidase B inhibitor, an anticholingergic, a COMT inhibitor or another medication such as rivastigmine tartrate or Amantadine.

The pharmaceutical composition of the present invention may include any additional components that are non-immunogenic and biocompatible with selenate, as well as capable of bioabsorption, biodegradation, elimination as an intact molecule. The formulation may be supplied in a ready-to-use form or may be supplied as a sterile powder or liquid requiring vehicle addition prior to administration. If sterility is desired, the formulation may be made under sterile conditions, the individual components of the mixture may be sterile, or the formulation may be sterile filtered prior to use. Such a solution can also contain appropriate pharmaceutically acceptable carriers, such as but not limited to buffers, salts, excipients, preservatives, etc.

In some embodiments, sustained release oral formulations are used for administering selenate or a pharmaceutically acceptable salt thereof in the methods of the invention. These formulations generally comprise selenate or a pharmaceutically acceptable salt thereof having decreased solubility in order to delay absorption into the bloodstream. In addition, these formulations may include other components, agents, carriers, etc., which may also serve to delay absorption of the selenate or a pharmaceutically acceptable salt thereof. Microencapsulation, polymeric entrapment systems, and osmotic pumps, which may or may not be bioerodible, may also be used to allow delayed or controlled diffusion of the selenate or a pharmaceutically acceptable salt thereof from a capsule or matrix.

The selenate or a pharmaceutically acceptable salt thereof can be used solus or as part of another agent. Accordingly, the present invention also contemplates an agent that comprises selenate or a pharmaceutically acceptable salt thereof for the treatment of a neurodegenerative disease.

In order that the nature of the present invention may be more clearly understood and put into practical effect, particular preferred embodiments thereof will now be described with reference to the following non-limited examples.

BRIEF DESCRIPTION OF THE FIGURES

FIG. 4A(ii) is a graphical representation showing the effects of sodium selenate on the concentration of inorganic phosphate released from a serine phosphopeptide by the phosphatase action of PP2A.

EXAMPLES

Example 1

Sodium Selenate Dephosphorylates Akt by an Indirect Mechanism

Figure 1:
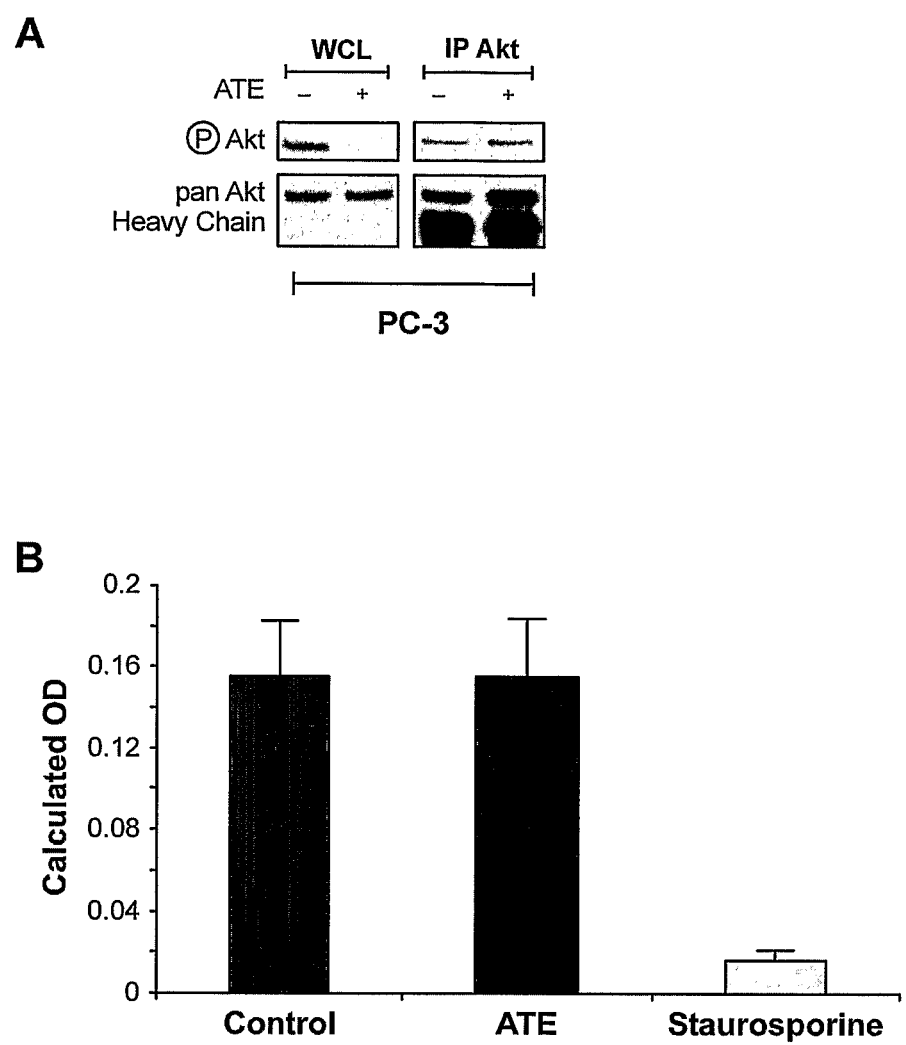
FIG. 1A is a comparative representation of the levels of phosphorylated Akt following treatment both in intact cells and in a cell free environment for PC3 cells.
FIG. 1B is a graphical representation comparing the effect of sodium selenate and staurosporine, a potent but non-specific protein kinase inhibitor, on the enzymatic activity of recombinant human Akt1 using Calbiochem K-LISA™ Akt activity kit.

Sodium selenate consistently induces the dephosphorylation of Akt in intact prostate carcinoma cells. Such dephosphorylation may be the result of a direct inhibitory effect on the Akt protein itself, or alternatively, can be similarly achieved indirectly by boosting a negative regulator or inhibiting a positive regulator of Akt phosphorylation. To distinguish between a direct and an indirect mechanism, the effect of sodium selenate on Akt phosphorylation and activity in a cell free environment was determined. PC3 prostate carcinoma cells were plated in 100 mm dishes, and when 70-80% confluent serum starved overnight. To determine the effect on Akt phosphorylation in intact cells, PC3 cells were treated with sodium selenate 500 µM in fresh serum free media for 1 hour. Cells were lysed, and the level of Akt Ser473 phosphorylation determined by immunoblot analysis with an activation specific antibody, and comparison made to levels of Akt protein expressed. To determine the effect on purified Akt, similarly plated but untreated PC3 cells were lysed in RIPA (minus phosphatase inhibitors), a stringent cell lysis buffer that minimizes maintenance of protein-protein complexes. Akt was purified from equal amounts (40-500 µg) of whole cell lysate (WCL) by immunoprecipitation with a pan-Akt monoclonal antibody, and then incubated with 500 µM sodium selenate for 1 h in a heat block at 37° C. The immunoprecipitated protein was then resolved and the level of activated Akt determined by immunoblot analysis as described above. FIG. 1A compares the levels of phosphorylated Akt following treatment both in intact cells and a cell free environment for PC3 cells. Treatment of intact PC3 cells with 500 µM sodium selenate for 1 h results in a profound reduction in Akt phosphorylation.

To confirm these findings, the effect of sodium selenate on the enzymatic activity of recombinant human Akt1 was measured using the Calbiochem K-LISA™ Akt activity kit, and compared it to the effect of staurosporine, a potent but non specific protein kinase inhibitor. This ELISA based assay uses a biotinylated peptide substrate (GRPRTSSFAEG) that is phosphorylated on the second serine by Akt. 250 ng of recombinant human Akt1 with or without sodium selenate 500 µM or staurosporine 1 µM was incubated with biotinylated-Akt substrate in streptavidin-coated wells for 30 min at 30° C. Bound phosphorylated substrate was then detected with a phospho-serine detection antibody, followed by the HRP-antibody conjugate, and colour development with TMB substrate. Absorbance measured at 450 nm with reference to 590 nm. The results of three independent experiments, summarised as mean calculated absorbance ($A_{450}$-$A_{590}$-blank) ±SEM, are shown in FIG. 1B. Consistent with the observations described above, sodium selenate had no measurable direct effect on the kinase activity of recombinant human Akt. In contrast, the non-specific inhibitor staurosporine potently inhibited the kinase activity of Akt.

In summary, these data indicate the sodium selenate has no direct inhibitory effect on Akt activity, indicating that the observed dephosphorylation must be via an indirect mechanism.

Example 2

Figure 2:
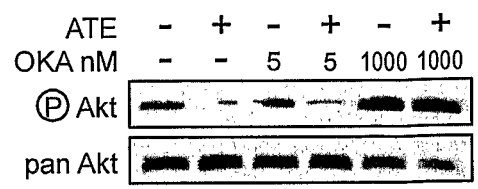
FIG. 2A is a comparative representation of Akt phosphorylation at $Ser^{473}$ in the presence of sodium selenate or okadaic acid, a polyether toxin from red-tide algae which inhibits phospho-protein phosphatases PP1 and PP2A.
FIG. 2B is a comparative representation of Akt phosphorylation at $Ser^{473}$ in the presence of sodium selenate or a number of phospho-protein phosphatase inhibitors, tautamycin, okadaic acid, endothall A, calyculin A and cyclosporine A.
FIG. 2C provides representations of immunoprecipitation of Akt from PC3 cells showing the amount of Akt complexed with PP2A in the absence (control) and presence of selenate (ATE) or fetal calf serum (FCS).
FIG. 2D is a graphical representation of phosphatase PP2A activity in PC3 cells in the presence or absence of sodium selenate.
Figure 2:
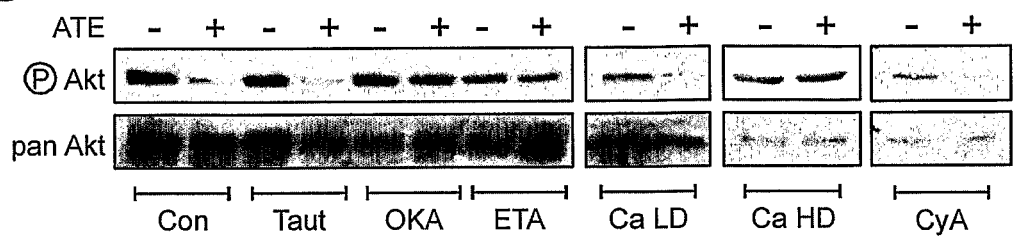
Figure 2:
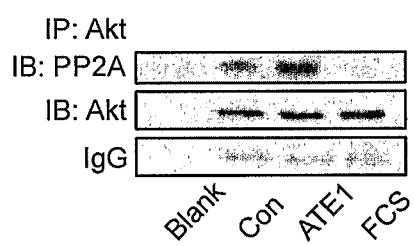
Figure 2:
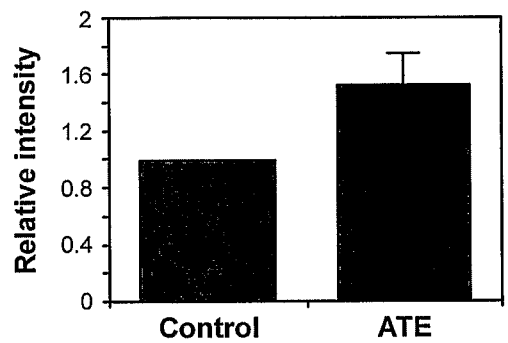
Figure 2:
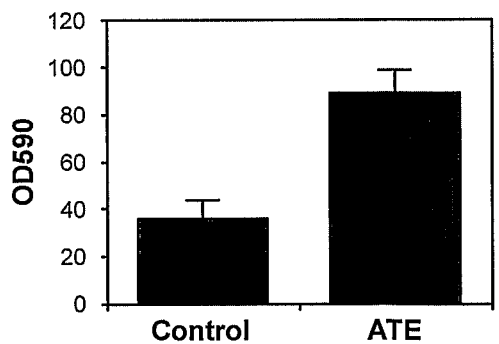

Sodium Selenate Dephosphorylates Akt by Stimulating the Phosphatase Activity of PP2A A reduction in net Akt activity could be achieved indirectly by either preventing the initial Akt phosphorylation, or alternatively, increasing Akt dephosphorylation [Kohn et. al. 1996]. However, given the biphasic response of Akt phosphorylation (an initial transient boost followed by a profound and sustained decrease) induced by sodium selenate, it seemed unlikely that sodium selenate was acting by simply decreasing the ability of an upstream kinase to phosphorylate Akt. The effect of protein phosphatase inhibition on the ability of sodium selenate to induce Akt dephosphorylation was therefore determined. Initially okadaic acid, a polyether toxin from red-tide algae (and causative agent of diarrhoetic shellfish poisoning) which inhibits the phospho-protein phosphatases PP1 and PP2A, two phosphatases implicated in the regulation of Akt dephosphorylation was used [Fernandez et al., 2002]. $5 \times 10^5$ PC3 prostate carcinoma cells were plated per well of a 6 well plate, allowed attach for 8 h, and then serum starved overnight. Cells were pretreated with or without okadaic acid 5 nM or 1000 nM for 30 min in fresh serum free media, and then sodium selenate added to a final concentration of 500 μM for 1 h. Lysed cells were resolved by SDS-PAGE, then probed for Akt phosphorylation at the Ser473 residue by immunoblot analysis with an antibody that specifically recognizes Akt when phosphorylated at this site, and comparison made with the total levels of Akt protein expressed (FIG. 2A). Treatment of the PTEN deficient PC3 cells with sodium selenate, as expected, markedly reduces the chronically high levels of Akt phosphorylation observed in this cell line, and this reduction is unaffected by prior incubation with 5 nM okadaic acid. In contrast, pre-treatment with 1000 nM of okadaic acid not only boosts Akt phosphorylation in non-selenate controls, but completely abolishes the inhibitory effect of sodium selenate.

To further refine the phosphatase involved, a broad panel of phospho-protein phosphatase (PPP) inhibitors, which differ in their specificities for PPP inhibition, were screened for their ability to abrogate the inhibitory effect of sodium selenate on Akt phosphorylation. This panel included tautamycin 500 nM (PP1), okadaic acid 500 nM (low dose PP2A>PP1), endothall A (PP2A) 100 μM, calyculin A 2 nM (low dose PP1>PP2A), calyculin A 10 nM (high dose inhibits PP1 and PP2A) and cyclosporine A 400 ng/ml (PP2B). PC3 prostate carcinoma cells were plated out essentially as described above, and similarly treated with sodium selenate 500 μM for 1 h with or without pretreatment with a PPP inhibitor for 30 min prior. Again, lysed cells were resolved by SDS-PAGE, then membranes probed for Akt phosphorylation at the Ser$^{473}$ residue by immunoblot analysis with an antibody that specifically recognizes Akt when phosphorylated at this site, and comparison made with the total levels of Akt protein expressed. As indicated in FIG. 2B, in cells that received no pretreatment with a PPP inhibitor, or in cells that were treated with PPP inhibitors that were specific for PP1 or PP2B, exposure to sodium selenate resulted in a marked decrease in the phosphorylation of Akt. In contrast, cells that were treated either with low dose okadaic acid or endothall A, specific or relatively specific inhibitors of PP2A, completely blocked sodium selenate induced Akt dephosphorylation.

Sodium selenate could increase the PP2A mediated Akt dephosphorylation either by increasing the rate of complex formation between PP2A and Akt, increasing the intrinsic phosphatase activity of PP2A already bound to PP2A, or both. To help distinguish between these mechanisms it was first determined if treatment with sodium selenate increases the level of complex formation between PP2A and Akt. $1 \times 10^6$ PC3 prostate carcinoma cells were plated onto 6 cm dishes, allowed attach for 8 h, and then serum starved overnight. Cells were then treated either with 500 μM sodium selenate in fresh serum free media, or 10% FCS, for 1.5 h, and then lysed in ELB buffer. Total Akt was immunoprecipitated from 400 μg of each whole cell lysate using a monoclonal anti-Akt antibody, and captured with protein A-sepharose beads. Negative control lysates (blank) had the immunoprecipitating antibody omitted. Following washing to reduce non-specific binding, the beads were boiled for 5 min in 3× SDS protein loading buffer, centrifuged at high speed and the supernatant resolved by SDS-PAGE. The level of PP2A binding was determined by immunoblot analysis with an antibody that specifically recognizes the catalytic subunit of the phosphatase, and comparison made with the amount of Akt pulled down and the concentration of precipitating antibody (IgG). As indicated in FIG. 2C, immunoprecipitation of Akt from untreated PC3 cells increases the amount of PP2A catalytic subunit detectable above that of non-specific binding to the beads (blank), indicating that even in the basal state with high levels of Akt phosphorylation, at least some Akt is complexed with PP2A. Treatment with sodium selenate increases the association of PP2A catalytic subunit with Akt, whereas stimulation with serum decreases complex formation to below basal levels. To quantify this increase in complex formation, representative immunoblots from three independent experiments were digitalized, subjected to densitometric analysis, and normalized to the control for each experiment. The mean ratio of PP2A catalytic subunit to total immunoprecipitated Akt protein ±SEM was then determined. As indicated in FIG. 2C, an approximately 50% increase in the binding of PP2A catalytic subunit to Akt protein following treatment with sodium selenate was observed.

To determine if the effects of sodium selenate on Akt dephosphorylation could be fully explained by a simple increase in association between the two proteins, the effect of sodium selenate on Akt-associated phosphatase activity was measured. $2 \times 10^6$ PC3 cells were plated in 10 cm plates, allowed to attach for 8 hours, and then serum starved overnight. Cells were then treated with or without sodium selenate 500 μM for 1 h in fresh serum free media, then lysed in a low phosphate buffer. 500-600 μg of total protein was then immunoprecipitated with anti-Akt (1:100) monoclonal antibody and 30 μl of Protein A slurry, and after washing, checked for free phosphate contamination by incubation of 25 μl of final wash buffer with Malachite Green. Immunoprecipitates were assayed for phosphatase activity by incubation with 500 μM synthetic phospho-threonine peptide for 10 min at 30° C. with agitation. Free phosphate was detected by the addition of malachite green solution, and absorbance was read at 590 nm, for each sample in duplicate. The mean phosphatase activity from three independent experiments ±SEM is shown in FIG. 2D. Treatment of PC3 cells with sodium selenate more than doubled the phosphatase activity associated with immunoprecipitated Akt protein, significantly greater than the simple increase in PP2A binding previously observed.

In summary, these data demonstrate that sodium selenate induces Akt dephosphorylation indirectly through a phosphoprotein phosphatase, specifically PP2A. Although sodium selenate increases the amount of PP2A binding to Akt, the relative increase in associated phosphatase activity is nearly twice that, indicating that sodium selenate may primarily affect enzyme activity.

Example 3

Sodium Selenate Directly Boosts the Phosphatase Activity of PP2A Core Dimer

Figure 3:
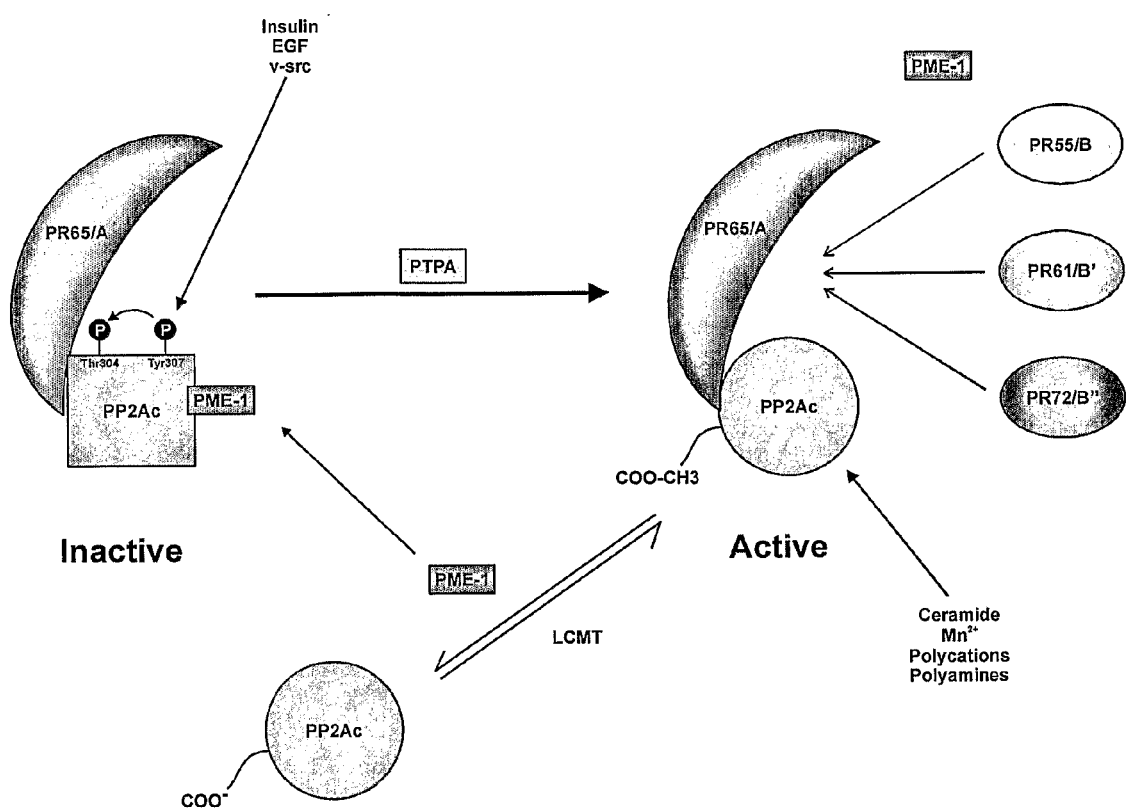
FIG. 3 is a schematic representation of the post-translational regulation of PP2A phosphatase activity and substrate specificity (LCMT—leucine carboxymethyltransferase, PME-1—phosphatase methylesterase 1, PTPA—Phospholyrosyl phosphatase activator).

The core structure of PP2A consists of 36 kDa catalytic subunit (PP2Ac) and a 65 kDa regulatory subunit (PR65 or A subunit). Binding with a third regulatory B subunit regulates substrate specificity [Wera and Hemmings, 1995]. PP2A phosphatase activity can be regulated by post-translational modification, represented schematically in FIG. 3. PP2Ac has been shown to be phosphorylated in vitro by both receptor and non-receptor tyrosine kinases such as EGFR, the insulin receptor, p60v-src and p561ck [Chen et al., 1992]. This phosphorylation occurs specifically at Tyr307, and is associated with a greater than 90% loss in phosphatase activity [Chen et al., 1992]. This phosphorylation is also identified in vivo, and is increased in fibroblasts stimulated with serum or EGF, or transformed with p60v-src, whereas it is decreased by serum starvation [Chen et al., 1994]. Phosphorylation of the adjacent Thr304 has also been associated with a significant loss of phosphatase activity [Guo and Damuni, 1993]. In contrast to Tyr307, it appears that Thr304 is phosphorylated by an auto-phosphorylation-activated protein kinase, thereby amplifying the initial inhibitory signal. In both cases, PP2A acts as its own phosphatase, as pharmacological inhibition with okadaic acid or microcystin-LR increases phosphorylation [Chen et al., 1994, Guo and Damuni, 1993]. Thus, following the removal of the inhibitory stimulus, PP2A hydrolyses both phosphate groups to rapidly regenerate active phosphatase. PP2Ac is also subject to regulation by reversible methylation of a carboxy terminal lysine residue, L309. The methylation reaction is catalysed by a leucine carboxyl methyltransferase [Xie and Clarke, 1994], and appears necessary for the correct association of subunits to form an active trimer [Wu et al., 2000, Tulstylch et al., 2000, Bryant et al., 1999]. PP2Ac is demethylated by phosphatase methylesterase 1 (PME-. 1) [Lee et al., 1996]. Interestingly, PME-1 has also been reported to bind to and potentially stabilize PP2a dimers and trimers in an inactive conformation, a situation reversed by phosphotyrosyl phosphatase activator (PTPA), a protein originally identified stimulating PP2A tyrosyl phosphatase activity [Cayla et al., 1994, Langin et al., 2004, Van Hoof et al., 2005].

To determine if the boost in PP2A phosphatase activity observed with sodium selenate was independent of an effect on upstream components involved in post-translational regulation, the enzymatic activity of human PP2A A-C heterodimer purified from red blood cells incubated in the presence or absence of sodium selenate was determined. In initial assays a chemical substrate of phosphatase enzymatic action, para-nitrophennylphosphate (pNPP) was used, which following hydrolysis of the phosphate moiety generates para-nitrophenol, an intensely yellow chromogen which is soluble under alkaline conditions. 0.05 U of purified human PP2A dimer was incubated in the presence of 5 mM sodium selenate or 500 nM okadaic acid for a total of 30 min at 37° C., and measured the amount of para-nitrophenol generated, as a readout of phosphatase activity, compared to untreated control samples. Absorbance of each sample was measured in duplicate at 405 nm with 590 nm as a reference. PP2A activity was calculated using the following equation:

$$\text{activity} = (\text{sample vol in liters}) \times A_{405} / 1.78 \times 10_4 M^{-1} \text{cm}^{-1} \text{ (extinction coefficient)} \times 0.25 \text{ cm} \times 15 \text{ minutes} \times 0.05 \text{ U enzyme}$$

Figure 4:
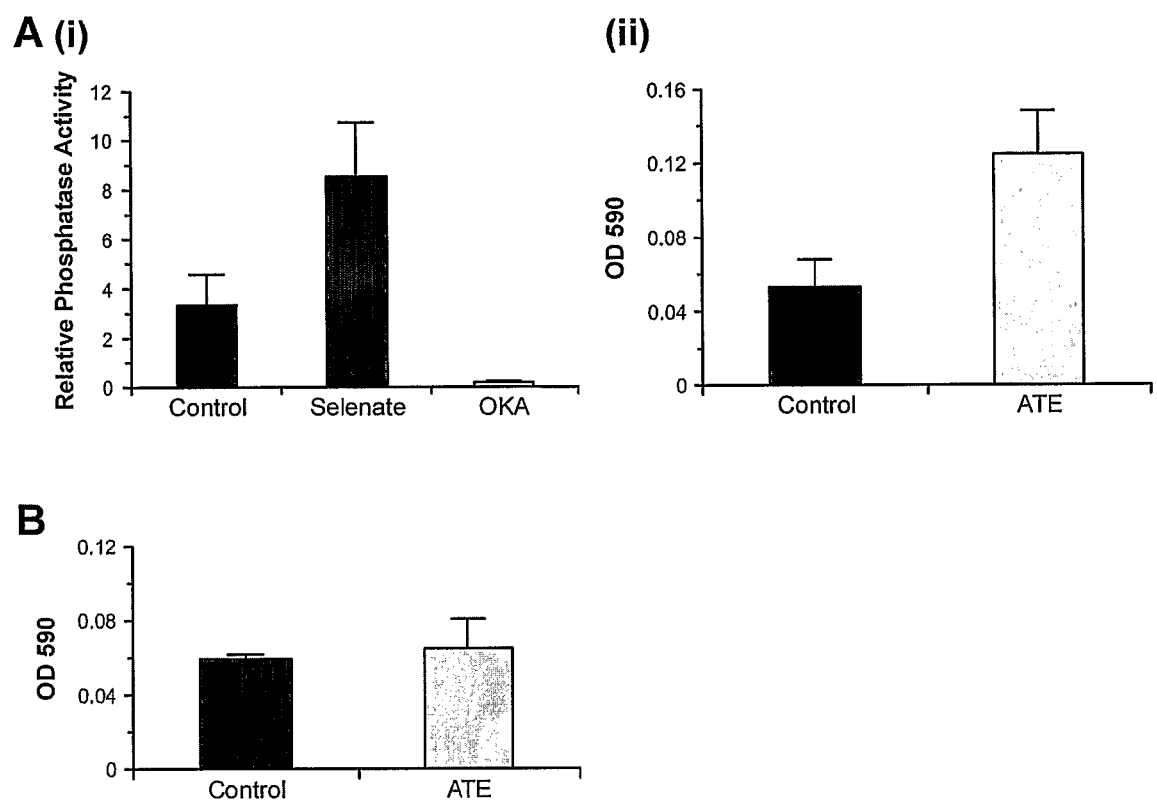
FIG. 4A(i) is a graphical representation of relative PP2A phosphatase activity in the absence (control) of, or in the presence of sodium selenate or okadaic acid (OKA).
FIG. 4B is a graphical representation showing the effects of sodium selenate on the phosphatase activity of PP1.

Data is presented as mean relative phosphatase activity ±SEM from at least three independent experiments. As indicated in FIG. 4A(i), even with such a low concentration of purified enzyme, phosphatase activity was readily apparent, and this was completely abolished by incubation with okadaic acid. In contrast, incubation of PP2A with sodium selenate nearly tripled the observed phosphatase activity.

It was next determined if this boost in phosphatase activity was substrate specific by measuring the effect of sodium selenate on the liberation by PP2A A-C dimer of inorganic phosphate from a synthetic 6 amino acid peptide, phosphorylated on an internal threonine residue. 0.01-0.05 U of PP2A was incubated with 500 μM of phosphopeptide for 15 min at 37° C., with or without 50 μM sodium selenate. The amount of inorganic phosphate released by enzymatic activity was determined by the addition of malachite green, and absorbance read at 590 nm. Malachite green forms a stable green complex in the presence of molybdate and orthophosphate, allowing the concentration of inorganic phosphate present to be measured. Data is presented as mean absorbance at 590 nm from at least three independent experiments, ±SEM. As indicated in FIG. 4A(ii), sodium selenate again more than doubled the concentration of inorganic phosphate released from the serine phosphopeptide by the phosphatase action of PP2A.

The catalytic subunit of PP1 shares approximately 50% sequence homology with the catalytic subunit of PP2A, the highest of any of the related phosphatases [Barton et al., 1994]. To determine if the boost in phosphatase activity stimulated by sodium selenate was specific to PP2A, its effect on the activity of PP1 was determined. 0.05 U of rabbit PP1 purified from skeletal muscle was incubated with 500 μM phospho-threonine synthetic peptide for 15 min at 37° C., with or without 50 μM sodium selenate, and the concentration of free phosphate determined using malachite green as described above. Data is presented as mean absorbance at 590 nm from three independent experiments, +SEM. As indicated in FIG. 4B, sodium selenate did not affect the phosphatase activity of PP1.

Example 4

Sodium Selenate Does Not Affect the Redox Regulation of PP2A

An increasing body of work suggests that reversible oxidation is a common mechanism by which protein phosphatases are negatively regulated [Wang et al., 1996, Barrett et al., 1999, Sohn and Rudolph 2003]. A conserved cysteine residue in the catalytic domain is critical to their enzymatic activity, but in an oxidating microenvironment this may be modified by the formation of either intramolecular disulphide or sulphenyl-amide bonds (FIG. 5A), with the loss of phosphatase activity [Salmeen et al., 2003, Kwon et al., 2004]. Given that selenium compounds can affect cellular redox state, the possibility that sodium selenate stimulated PP2A by relieving the inhibitory effects of oxidation was investigated.

Figure 5:
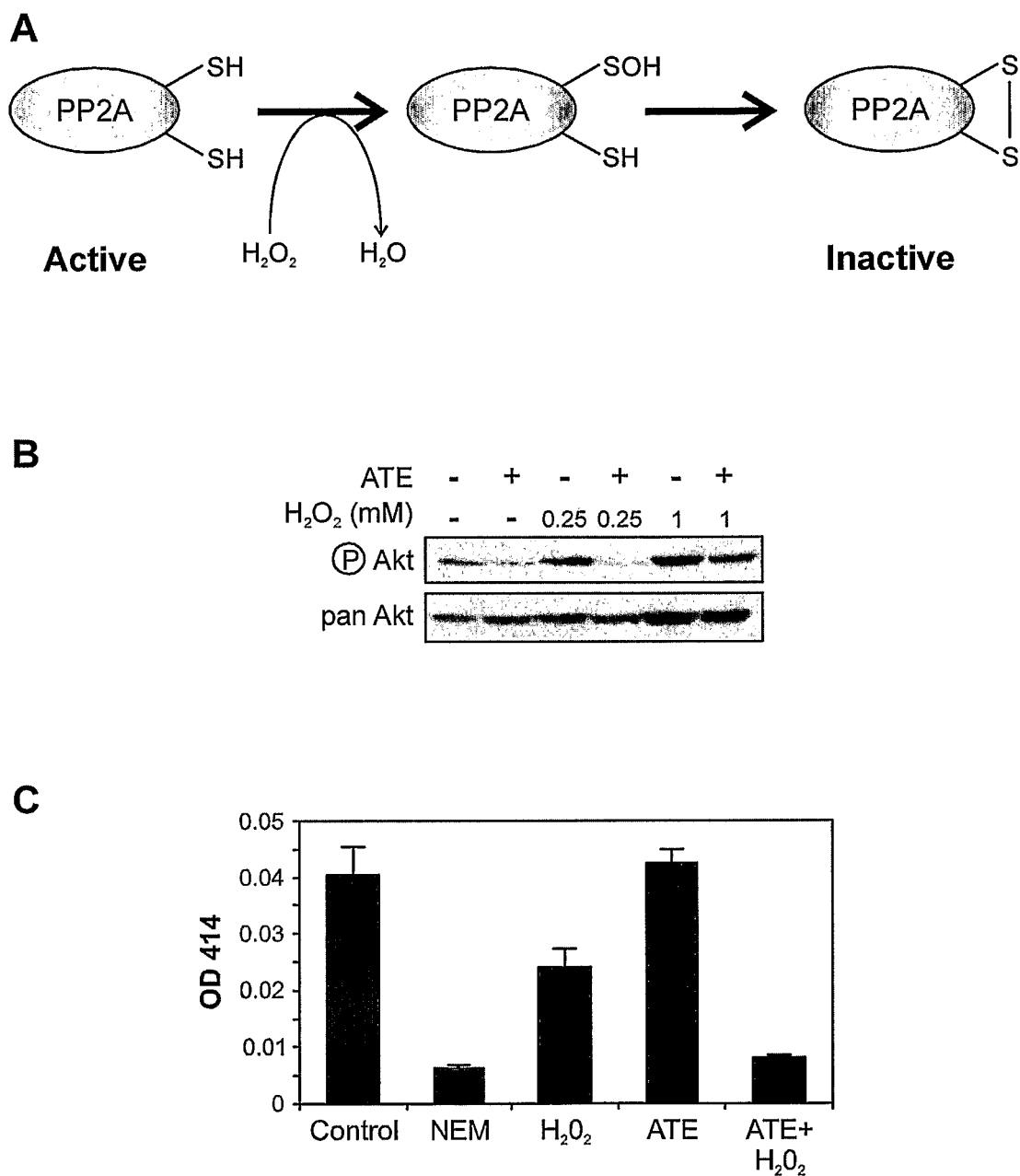
FIG. 5A is a schematic representation of the inactivation of PP2A in an oxidising environment.
FIG. 5B is a representation showing the effects of sodium selenate and hydrogen peroxide on the level of Akt phosphorylation.
FIG. 5C is a graphical representation of the free sulfhydryl groups present in the PP2A phosphatase in the presence of N-ethylmeleimide (NEM), hydrogen peroxide, sodium selenate and sodium selenate together with hydrogen peroxide.
FIG. 5D is a graphical representation of fluorescence distribution histogram for cells treated with sodium selenate or N-acetyl cysteine (NAC) with or without hydrogen peroxide.
FIG. 5E graphically represents the mean percentage of fluorescent cells upon treatment with hydrogen peroxide, sodium selenate, hydrogen peroxide and sodium selenate, NAC, and hydrogen peroxide and NAC.
Figure 5:
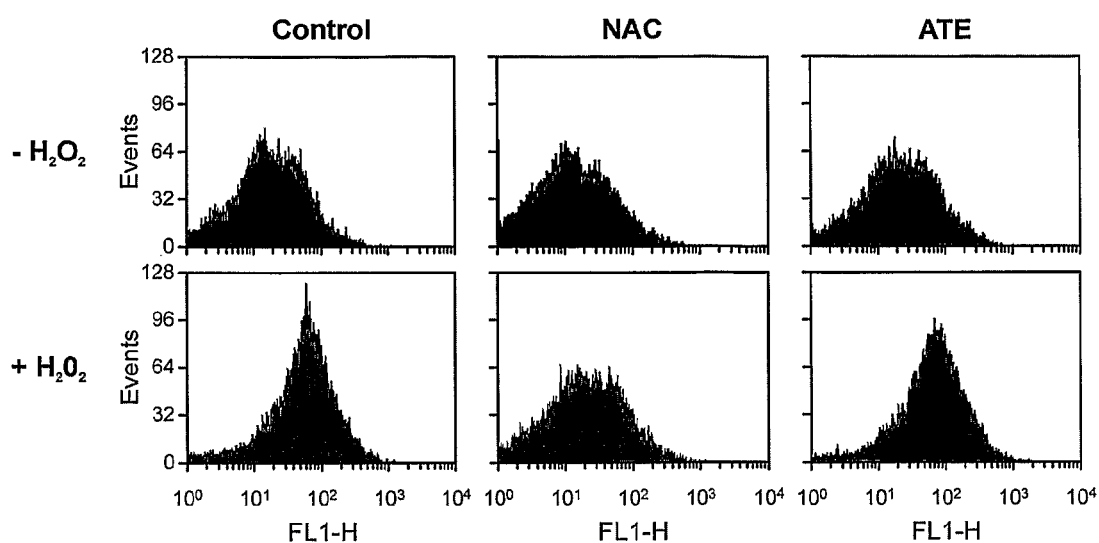
Figure 5:
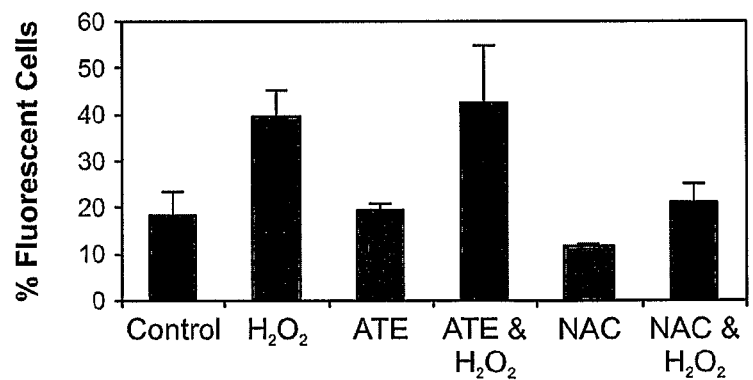

Initially it was determined if the dephosphorylation of Akt induced by sodium selenate was sensitive to the cellular redox state. $5\times10^5$ PC3 prostate carcinoma cells were plated per well in a 6-well plate, allowed to attach for 8 h, and then serum starved overnight. Cells were treated with or without 500 µM sodium selenate in fresh media, and then exposed to hydrogen peroxide at 0.25 mM or 1 mM for 10 min. Equal amounts of whole cell lysates were resolved, and then subjected to immunoblot analysis to determine the level of phosphorylated Akt Ser$^{473}$. Comparison was then made with the total level of Akt protein expressed. As indicated in FIG. 5B, treatment of cells with sodium selenate markedly reduced the level of Akt phosphorylation, and this was unaffected by the acute addition of 0.25 mM of hydrogen peroxide. In contrast, acute exposure to a higher dose of 1 mM hydrogen peroxide completely abolished the dephosphorylating effect of sodium selenate, indicating that this block is redox sensitive.

Inactivating reversible oxidation of protein phosphatases involves the modification of a critical cysteine residue within the catalytic domain, ultimately leading to the formation of either intramolecular disulphide or sulphenyl-amide bonds. To determine if sodium selenate had any modifying effect on cysteine residues in PP2A, the number of free sulfhydryl groups in purified human PP2A A-C dimer was quantified following various treatments using Ellman's assay [Ellman, 1958]. Ellman's reagent (5,5'-Dithio-bis(2-nitrobenzoic acid), DTNB) rapidly forms a disulphide bond with free sulfhydryl groups with the release of chromogenic thiolate ions. 0.01 U of PP2A was incubated with N-ethylmaleimide (NEM) 10 mM or hydrogen peroxide 10 mM or sodium selenate 10 mM, or sodium selenate 10 mM and hydrogen peroxide 10 mM for 15 min at 37° C. The quantity of free sulfhydryl groups present within the phosphatase was then determined by the addition of Ellman's reagent and subsequent measurement of absorbance at 412 nm (FIG. 5C). Incubation with both NEM, a sulfhydryl alkylating agent, and hydrogen peroxide significantly reduced the number of free sulfhydryl groups present. In contrast, incubation with sodium selenate has no effect, and in particular, did not protect PP2A from hydrogen peroxide mediated modification of sulfhydryl groups. Indeed, the modification of sulfhydryl groups by hydrogen peroxide was significantly more efficient in the presence of sodium selenate.

Next it was determined if sodium selenate affected the redox potential of intact cells using 2',7'-dichlorodihydrofluorescein diacetate (DCFDA). DCFDA is non-fluorescent and freely cell permeable, but in the presence of reactive oxygen species (ROS) is rapidly converted to the cell impermeable but highly fluorescent 2',7'-dichlorofluorescein (DCF) [Bass et al., 1983]. $1\times10^6$ PC3 prostate carcinoma cells were plated in 60 mm dishes, allowed to attach for 8 h, and serum starved overnight. Cells were incubated with DCFDA 5 µM for 15 min prior to treatment.

Cells were treated with either 500 µM of sodium selenate or 1 mM of N-acetylcysteine (NAC) for 1 h, and then exposed to 500 µM of hydrogen peroxide for 10 min. The proportion of fluorescent cells was then determined by flow cytometry. FIG. 5D shows a representative fluorescence distribution histogram for each treatment group, and the mean percentage of fluorescent cells from three independent experiments +SEM is summarized in FIG. 5E. Exposure of PC3 cells to hydrogen peroxide lead predictably to a marked increase in the generation of intracellular oxygen free radicals, indicated by a shift to the right in the distribution histogram. Pretreatment of the cells with sodium selenate had no effect on the basal proportion of fluorescent cells, and did not protect the cells from the generation of ROS following exposure to hydrogen peroxide. In contrast, pretreatment with the hydrogen donor NAC lead to a small reduction in the basal proportion of fluorescent cells, and in particular, significantly attenuated ROS production by hydrogen peroxide.

In summary, these data indicate that although the dephosphorylation of Akt induced by sodium selenate is sensitive to the cellular redox state, sodium selenate does not boost the phosphatase activity of PP2A by relieving intrinsic but reversible inhibitory oxidation.

Example 5

Sodium Selenate Stimulated PP2A Phosphatase Activity Demonstrates Substrate Specificity PP2A is a ubiquitous and highly expressed protein that is estimated to make up between 0.1-1% of total cellular protein [Gallego M and Virshup 2005; Cohen, 1997] and has been implicated in the regulation of an ever increasing number of protein substrates [Zhu et al., 2004; Woetmann et al., 2003; Silverstein et al., 2002]. The mechanism which controls PP2A substrate specificity is incompletely understood, but differential binding of specific regulatory B subunits appears to be important [Van Kanegan et al., 2005]. It was determined if the increased PP2A phosphatase activity stimulated by sodium selenate was indiscriminate, or specific to a particular heterotrimer.

Figure 6:
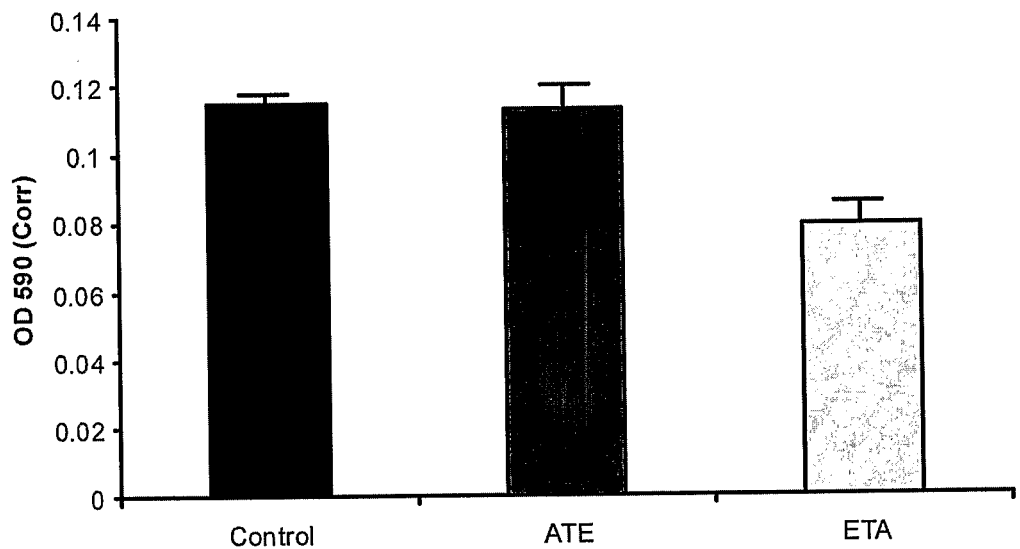
FIG. 6A graphically represents the relative phosphatase activity of immunoprecipitated PP2A with sodium selenate (ATE 500 µM) or endothall A (ETA 100 µM) or without an additive (control).
FIG. 6B is a comparative representation of levels of phosphorylated p70S6K following treatment with LY294003 (LY 50 µM) or sodium selenate (ATE 500 µM), with our without pre-treatment with okadaic acid (OKA 500 nM).
FIG. 6C is a comparative representation of the probing of different B family subunits (B and B') of PP2A with antibodies that recognize Akt. Akt co-precipitated only with the B family subunit of PP2A.
Figure 6:
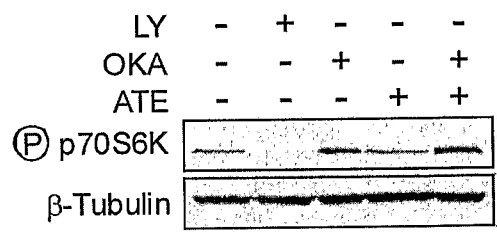
Figure 6:
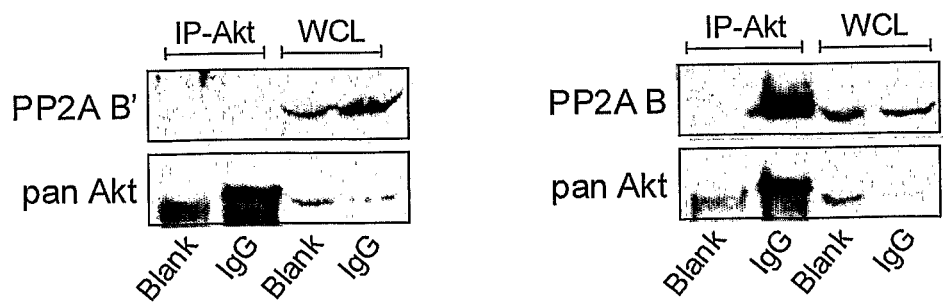

It has been demonstrated above that sodium selenate increases the phosphatase activity associated with Akt immunoprecipitated from PC3 prostate carcinoma cells, and that sodium selenate directly stimulates the phosphatase activity of purified PP2A A-C dimer. To determine if this boost in phosphatase activity is generalized, PP2A was immunoprecipitated from PC3 cells treated with either sodium selenate 500 µM or endothall A 100 µM for 1 hour using a monoclonal antibody to the PP2A catalytic subunit. Free phosphate was removed by passing cell lysates through desalting columns, and measured phosphatase activity using a phosphor-serine peptide and malachite green. The relative phosphatase activity of immunoprecipitated PP2A under the different conditions is shown in FIG. 6A as the mean absorbance of three independent experiments +SEM. The treatment of PC3 cells with sodium selenate had no effect on the phosphatase activity of the general pool of intracellular PP2A. In contrast, treatment with the PP2A specific phosphatase inhibitor endothall A significantly reduced phosphatase activity.

The effect of sodium selenate on another known substrate of PP2A, p70S6K was examined [Peterson et al., 1999]. $5\times10^5$ PC3 prostate carcinoma cells were plated per well of a 6-well plate, allowed to attach for 8 hours, then serum starved overnight. Cells were then treated with either LY294003 50 µM or sodium selenate 500 µM for 1 hour, with or without pre-treatment with okadaic acid 500 nM for 30 minutes prior. Equal amounts of whole cell lysates (75 µg) were resolved by SDS-PAGE, and the level of p70S6K phosphorylation determined by immunoblot analysis with an antibody that specifically recognizes the p70S6K protein when phosphorylated on Thr389. Comparison is made with the protein loading control β tubulin. As indicated in FIG. 6B, even under basal conditions, p70S6K phosphorylation is readily apparent, and this is abolished by treatment with the PI3K inhibitor LY294002. Consistent with its known role as a negative regulator of p70S6K phosphorylation, inhibition of PP2A with okadaic acid boosts the level of phosphorylation observed. However, in contrast to the dephosphorylation of Akt induced by sodium selenate, the phosphorylation of p70S6K is unaffected in similar conditions.

The primary determinant of substrate specificity appears to reside in the regulatory B subunit, which along with the A and catalytic subunits, comprises the trimeric complex observed in vivo.

An attempt was made to determine which family of B subunits formed a complex with Akt in prostate carcinoma cells. $2 \times 10^6$ PC3 prostate carcinoma cells were plated into 100 mm dishes, allowed to attach for 8 hours, and serum starved overnight. Cells were then lysed with ELB, a mild detergent buffer, and total Akt immunoprecipitated from 500 µg of lysate with a pan-Akt monoclonal antibody (1:100) and 30 µL protein A-sepharose. Negative controls (blank) had the immunoprecipitating antibody omitted. Following repeated washing the beads were boiled in 3× SDS protein loading buffer for 5 minutes, centrifuged at high speed, and the resulting supernatant resolved by gel electrophoresis. 100 µg of whole cell lysate was run out on the same gel for comparison, and the resulting membranes probed with antibodies that specifically recognize members of either B or B' families of subunits. Successful pulldown of Akt was confirmed by probing the same blots with an antibody that recognizes pan-Akt. As shown in FIG. 6C only a B family regulatory subunit co-precipitated with Akt in this system, suggesting that a trimer of PP2Ac, A and member of the R2 B subunit family mediates Akt dephosphorylation in these cells.

Example 6

Figure 7:
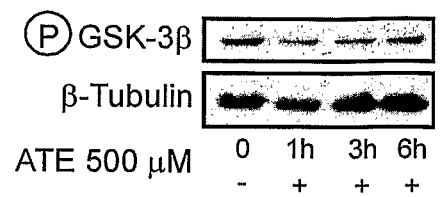
FIG. 7 is a representation showing the effects of sodium selenate on GSK3β activation.

The metabolic effects of insulin on glycogen synthesis are mediated by glycogen synthase kinase-3 (GSK-3), a direct downstream substrate of Akt. GSK-3 is a ubiquitously expressed serine/threonine kinase that phosphorylates and inactivates glycogen synthase. In response to activation of the insulin receptor, Akt phosphorylates and inactivates the repressor GSK-3, thereby stimulating glycogen synthesis [Cross et al., 1995]. In addition, GSK-3 has been implicated in the control of protein translation, cell cycle progression and Wnt signalling [Diehl et al., 1998, Welsh et al., 1996, He et al., 1995]. To determine the effect of sodium selenate treatment on GSK-3β activation, PC3 prostate carcinoma cells were plated, serum starved overnight, then treated with sodium selenate 500 µM in fresh media for various times as indicated (FIG. 7). Resolved whole cell lysates were subjected to immunoblot analysis with an antibody that specifically recognizes GSK-3β only when phosphorylated at Ser9, a site critical for its kinase activity, and comparison made with the cytoskeletal protein β-tubulin as a loading control. PC3 cells have high basal levels of GSK-3β activation, indicated by the high degree of phosphorylation observed in the control lane (0 h). Treatment with sodium selenate led to a marked reduction in phosphorylation, which was maximal at 1 h and 3 h, and returned towards basal levels at the 6 h timepoint. To quantify the degree of inhibition that sodium selenate induced, digitalized immunoblots were prepared comparing the effects of sodium selenate 500 µM for 3 h to LY294002 50 µM for 1 h and determined the degree of GSK-3β phosphorylation as a proportion of expressed protein by densitometry. On average, sodium selenate reduced GSK-3β by over 20%, whereas LY294002 resulted in an almost 60% reduction in phosphorylation levels.

Example 7

Sodium Selenate, but not Selenomethionine, Potently Inhibits Akt/Protein Kinase B Activation To determine whether sodium selenate can interfere with the activity of the PI3K pathway, serum free PC3 cells were treated with 500 µM sodium selenate for various times. The phosphorylation status of Akt in whole cell lysates was determined using activation specific antibodies. Because of the loss of PTEN, even in the absence of additional serum, there is robust activation of Akt at both the Ser473 and Thre308 sites. Addition of sodium selenate induced a transient boost in phosphorylation of Akt at both sites within 10 minutes of exposure. This boost was then followed by a marked and prolonged deactivation, whilst total cellular Akt levels (pan Akt) remained essentially unchanged.

Figure 8:
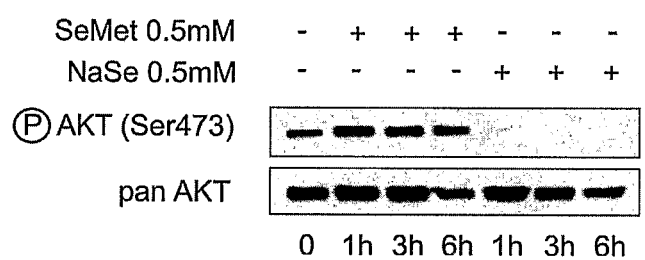
FIG. 8 is a comparative representation showing the selenomethionine did not affect the level of Akt phosphorylation whereas selenate inhibited Akt phosphorylation.

The effect of sodium selenate on Akt activation in PC3 cells was compared to that of selenomethionine, by treating with 500 µM of each compound for various timepoints and assessing Akt phosphorylation at Ser473. As indicated in FIG. 8, selenomethionine did not affect the level of phosphorylation of Akt at all time periods measured, whereas sodium selenate profoundly inhibited Akt phosphorylation.

Example 8

The Ability to Induce Akt Dephosphorylation is Unique to Sodium Selenate

Figure 9:
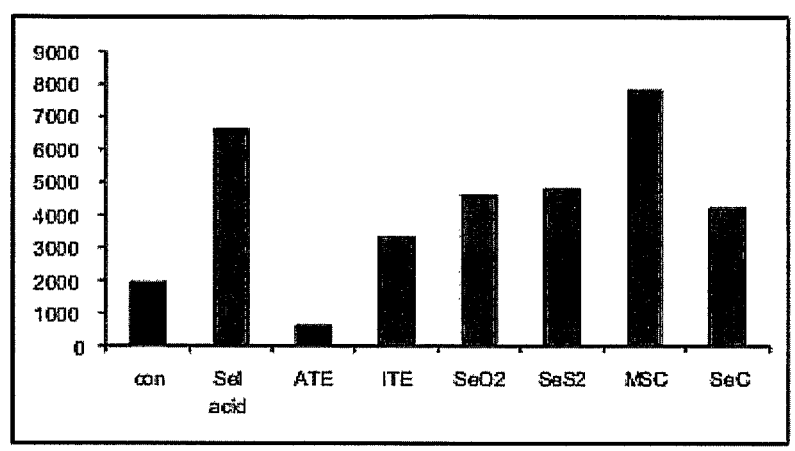
FIG. 9 is a graphical representation showing the effects of different selenium compounds on activation of Akt. Treatments: control (con); sodium selenate (ATE); Selenous acid (Sel acid); sodium selenite (ITE); selenium dioxide ($SeO_2$); selenium sulfide ($SeS_2$); methyl selenocysteine (MSC); and selenocysteine (SeC). Relative active Akt signal intensity correlated to total Akt protein levels is depicted on the y-axis. The graph indicates that only sodium selenate (ATE) inhibits activation of Akt, reducing levels of phosphorylated Akt below control (con) levels. In contrast, selenous acid (Sel acid), sodium selenite (ITE), selenium dioxide ($SeO_2$), selenium sulfide ($SeS_2$), methyl selenocysteine (MSC), selenocysteine (SeC) all induce activation of Akt above control (con) levels.

Given that sodium selenate consistently induced profound dephosphorylation of the key kinase Akt, whilst selenomethionine had no effect, it was determined if this ability was unique to sodium selenate or was shared by other chemical forms of selenium. Other inorganic (sodium selenite, selenium dioxide, selenium sulphide and selenious acid) and organic (methylselenocysteine, selenocystine) selenium species were tested for their ability to affect Akt activation. All forms were dissolved in water with the exception of selenium sulphide which was solubilised in DMSO, and added to serum starved PC3 cells at a concentration of 500 µM for 1 hour, Whole cell lysates were then resolved, and the activation status of Akt determined by immunoblotting with an antibody that specifically recognizes Akt when phosphorylated at the Ser473 site, as well as the total level of Akt expression (pan Akt). To quantify the degree of Akt activation, immunoblots were digitalised, and the ratio of phosphorylated Akt to total Akt determined by densitometry. The mean ratio of phosphorylated Akt to total Akt protein levels ±SEM from three independent experiments summarized in FIG. 9. Treatment of PC3 cells with sodium selenate at 500 µM for 1 hour resulted in a greater than 80% reduction in Akt phosphorylation at Ser473 compared to untreated cells ($p<0.05$, Students t-test). In contrast, treatment of PC3 cells with other inorganic and organic forms of selenium administered under identical conditions had no significant effect on the degree of Akt activation. In summary, these data indicate that the ability to induce Akt dephosphorylation is unique to sodium selenate.

Example 9

The ability to Enhance PP2A Activity is Unique to Sodium Selenate

Figure 10:
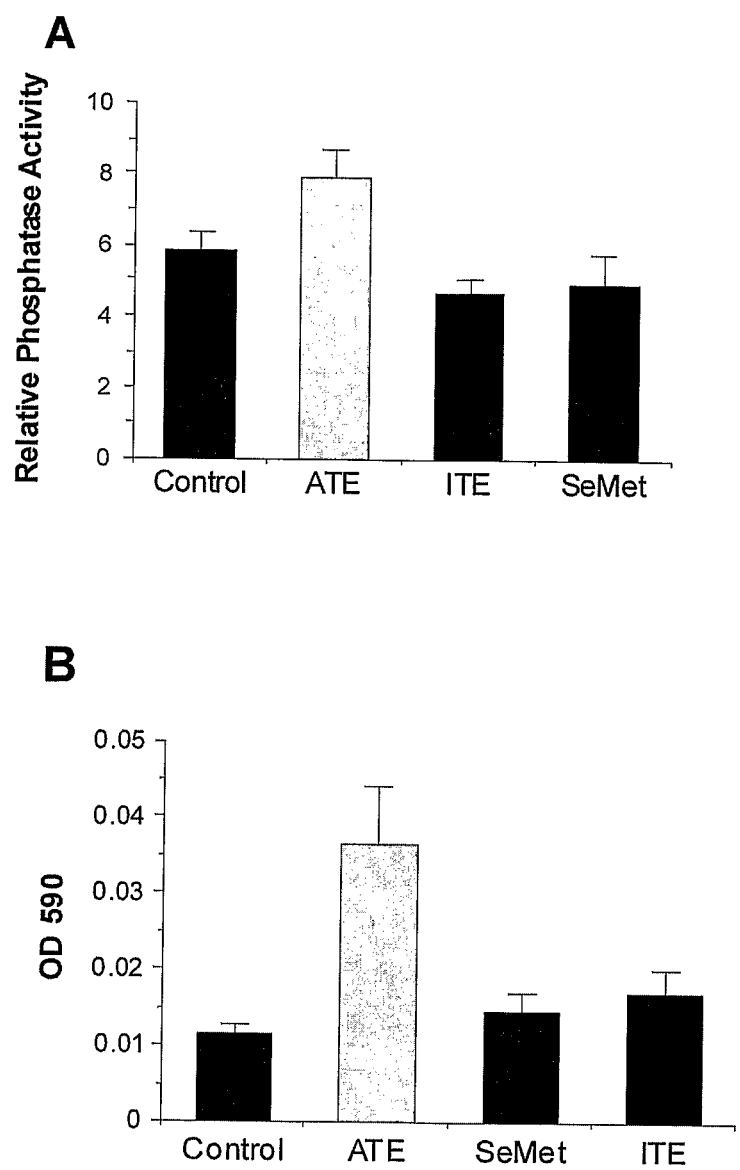
FIGS. 10A and 10B graphically represent the effect of sodium selenate (ATE), sodium selenite (ITE) and selenomethionine (SeMet) on PP2A phosphatase activity in the pNPP hydrolysis assay using pNPP (FIG. 10A) or a serine phosphopeptide (FIG. 10B) as a substrate.

In Example 7, data demonstrating of all of the chemical forms of selenium tested, sodium selenate alone significantly induced dephosphorylation of Akt was presented. To determine if a differential effect on PP2A activity could explain this specificity, the effect of sodium selenate (5 mM or 50 µM), sodium selenite (5 mM or 50 µM) and selenomethionine (5 mM or 50 µM) on PP2A phosphatase activity was compared in the pNPP hydrolysis assay using pNPP and a serine phosphopeptide as a substrate respectively (FIGS. 10A and 10B). In contrast to the clear boost in phosphatase activity observed with sodium selenate, neither sodium selenite nor selenomethionine significantly affected PP2A phosphatase activity.

Materials and Methods for Examples 1 to 9

Reagents
Cell Lines

The details of the mammalian cell line used in the experimental procedures is given in Table 1.

TABLE 1

| Cell Line | Origin | Source | Reference |
|---|---|---|---|
| Pc3 | Derived from bone metastasis of a grade IV prostatic adenocarcinoma from a 62-year-old male Caucasian | ATCC | (Kaighn ME et al., 1979) |

All cell cultures were maintained in a Forma Scientific Incubator with 5% or 10% carbon dioxide at 37° C. in RPMI 1641 with L-Glutamine (Gibco Invitrogen #11875-119). Penicillin (100 U/ml), streptomycin (100 µg/ml) and amphotericin B (25 ng/ml) (Gibco Invitrogen #15240-062) were added to media as standard. As a routine, cells were maintained in the presence of 5% or 10% fetal bovine serum (Gibco Invitrogen #10099-141) unless otherwise stated. Subconfluent cells were passaged with 0.5% trypsin-EDTA (Gibco Invitrogen #15400-054).

Commercially Available Antibodies

A number of commercially available primary and horseradish peroxidase (HRP) conjugated or fluorescently labelled or biotinylated secondary antibodies were used in the experimental work described, the details of which are summarized below:

Anti-Akt antibody rabbit polyclonal, Cat No. 9272, Cell Signalling Technology (CST);
Anti-Akt (5G3) mouse monoclonal, Cat No. 2966, CST;
Anti-phospho Akt (ser473) rabbit polyclonal, Cat No. 9271, CST;
Anti-phospho GSK3p (ser9) rabbit polyclonal, Cat No. 9336, CST;
different anti-PP2A antibodies, Cat Nos. 05-421, 06-2221, 07-334 and 05-592, Upstate.

Kinases and Kinase Inhibitors, Phosphatase Inhibitors and Purified Phosphatases

TABLE 2 kinase and phosphatase inhibitors

| | Name | Enzyme inhibited | Source | Cat No. | Diluent | Stock Conc. | Working Conc. |
|---|---|---|---|---|---|---|---|
| Kinase inhibitor | LY294002 | PI2K | Promega | V1201 | DMSO | 50 mM | 10-50 µM |
| Phosphatase inhibitor | tautomycin | PP1 | Biomol | 109946-35-2 | ethanol | 500 µM | 500 µM |
| Phosphatase inhibitor | endothall | PP2A | Calbiochem | 324760 | $H_2O$ | 100 mM | 100 µM |
| Phosphatase inhibitor | calyculin A | PP2A = PP1 | Calbiochem | 208821 | DMSO | 80 µM | 10 nM |
| Phosphatase inhibitor | okadaic Acid | PP2A >> PP1 | Calbiochem | 495604 | ethanol | 50 mM | 500 nM |
| Phosphatase inhibitor | cyclosporin A | PP2B | Calbiochem | 239835 | DMSO | 400 µg/mL | 400 ng/mL |

TABLE 3 purified phosphatases and recombinant kinases

| | Name | Species | Source | Cat. No. | Working Conc. |
|---|---|---|---|---|---|
| Purified phosphatase | PP2A | Human | Upstate | 14-111 (lot #28002) | 0.01-0.05U |
| Purified phosphatase | PP1 | Rabbit | Upstate | 14-110 (lot #26200) | 0.05U |
| Recombinant kinase | Akt1 | Human | Upstate | 14-276 (lot #25089BU) | |

Buffers, Solutions and Media

All solutions were stored at room temperature (RT) unless otherwise stated.

| | |
|---|---|
| EDTA 0.5 M | 186.1 g $Na_2EDTA \cdot 2H_2O$ dissolved in 1 litre $dH_2O$, pH adjusted to 8.0 with NaOH |
| Egg Lysis Buffer (ELB) | 250 mM NaCl, 50 mM Hepes pH 7.0, 5 mM EDTA, 1 mM DTT, 10% Triton-X100 |
| NaCl 5 M | 292.2 g NaCl dissolved in 1 litre $dH_2O$, autoclaved |

| | |
|---|---|
| PBS | NaCl 8.0 g, KCl 0.2 g, $Na_2HPO_4$ 1.44 g, $KH_2PO_4$ 0.24 g, made up to 1 litre, pH to 7.4 |
| RIPA lysis buffer | 10% Glycerol, 20 mM Tris-HCl pH 7.5, 2 mM EDTA, 1% Triton-X100, 1% NP40, 137 mM NaCl, 0.1% SDS. Made up fresh on ice. |
| SDS 20% | 200 g SDS dissolved in 1 litre $dH_2O$ |
| SDS-PAGE Running Gel | 0.375 M Tris pH 8.8, 0.1% SDS, APS, TEMED and 6-14.5% acrylamide |
| SDS-PAGE Sample Buffer 4X | 15% glycerol, 0.6 M 2-mercaptoethanol, 2% SDS, 62.5 mM Tris-HCl pH 6.8 and 0.1% w/v bromophenol blue |
| SDS-PAGE Stacking Gel | 0.125 M Tris pH 6.8, 0.1% SDS, 4.8% acrylamide (Biorad), ammonium persulphate (APS) and TEMED |
| SDS-PAGE Running Buffer | 9 g Tris base (25 mM) pH 8.3, 43.2 g Glycine (0.19 M) and 3 g SDS (0.1%) made up to 500 ml in $dH_2O$ |
| TBS 10X | 80 g NaCl, 2 g KCl, 30 g Tris pH 7.4 made up to 1 litre in $dH_2O$ |
| TBS-T 0.1% | 500 ml of TBS 10x, 5 ml Tween-20 made up to 1 litre in $dH_2O$ |
| Tris-HCl | 121.1 g Tris dissolved in 1 litre $dH_2O$, pH adjusted to 6.0-8.8 with concentrated HCl, autoclaved |
| Western Transfer Buffer | 14.4 g glycine, 3.03 g Tris, 800 ml $dH_2O$ and 200 ml methanol |
| Western Transfer Buffer | 3.03 g Tris base, 14.4 g Glycine in 800 ml $dH_2O$ with 200 ml methanol |
| Western Sample Buffer 4X | 1 ml of 0.5 M Tris pH 6.8, 800 µl glycerol, 800 µl 20% SDS, 400 µl β-mercaptoethanol, 400 µl 1% bromophenol blue |

Selenium Compounds

Sodium selenate was purchased from Sigma. All solutions were made freshly in $dH_2O$ and used at the stated concentrations.

Protein Expression

SDS-Polyacrylamide Gel Electrophoresis (SDS-PAGE)

Following specified treatments, cells in culture were washed once in PBS and then lysed for 15 min at 4° C. in either Egg Lysis Buffer (ELB) or RIPA lysis buffer containing a protease inhibitor cocktail (Calbiochem Protease Inhibitor Cocktail Set 1 #539131) and phosphatase inhibitors (10 mM Sodium Orthovanadate and 10 mM Sodium Fluoride) with the aid of a cell scraper. Samples were clarified by centrifugation at 14,000 rpm for 15 min at 4° C. and the supernatant used for analysis. Sample protein concentration was determined by Bicinchoninic Acid Solution Assay (BCA). 1 µl of lysate was diluted 1:25 with $dH_2O$ in a 96-well plate. 200 µl of an 80:1 solution of bicinchoninic acid solution and 4% (w/v) copper sulphate was added to each sample and incubated at 37° C. for 30 min. Absorbance was measured at 590 nm (Perkin Elmer MBA2000) against a series of protein standards.

Protein samples were analysed by gel electrophoresis using denaturing SDS-polyacrylamide gels, consisting of a stacking gel and a resolving gel. 50-100 µg of protein was loaded on SDS-PAGE gels of varying concentrations. SDS sample buffer was added in equal volume to the samples and boiled at 100° C. for 5 min prior to loading. Gel electrophoresis was performed in running buffer at approximately 100 V. The molecular weight of proteins of interest was assessed by protein size markers (Biorad Kaleidoscope) loaded with each gel.

Western Blot Analysis

Following resolution proteins were transferred to PVDF membrane (Immobilon P, Millipore). The membrane was prepared by immersion in 100% methanol for 10 s, rinsed in distilled water and equilibrated in western transfer buffer. Transfer occurred at 100 V at RT for 1.5 h or overnight at 4° C. The membrane was washed for 5 min in TBS-T and allowed to dry for 1 h. The membrane was then blocked with 3% skim milk in TBS with 0.1% Tween for 1 h at RT. The membrane was washed three times for 5 min with TBS-T and then incubated with the primary antibody diluted in 3% skim milk/0.1% TBS-T or 3% BSA/0.1% TBS-T for 1-2 h at RT or overnight at 4° C. with gentle agitation. Following three 5 min washes in 0.1% TBS-T the membrane was incubated with horseradish peroxidase conjugated secondary antibodies in blocking buffer for 1 h. The membrane was again washed three times for 5 min before antibody binding was detected by enhanced chemiluminescence with Super Signal® West Dura Extended Duration Substrate (Pierce #34075) or ECL Western Blotting Detection Agents (Amersham Biosciences #RPN2106). The luminescence was recorded by autoradiography using CL-exposure film Kodak). After initial analysis immunoblots were stripped with Membrane Stripping Buffer (62.5 mM TRIS pH7, 2% SDS, 7% β-mercaptoethanol) for 15 min at 60° C., washed three times in TBS-T and blocked again before reprobing.

Densitometric Analysis

Relevant immunoblots were converted to .tif files in Corel Photo-Paint Version 8 (Corel Corporation) using a Vista digital scanner (Umax). Densitometric analysis was performed in Image-Pro-Plus V4.5.1.22 for Windows (Media Cybernetics). Using a linear calibration in which white was assigned the value 0 and black the value 255, a region of interest corresponding to the relevant band was selected and signal intensity determined.

Immunoprecipitation 100-600 µg of whole cell lysate was incubated with various antibodies at a 1:100 dilution in microfuge tubes on a rotating wheel for 1-2 h at RT or 16 h at 4° C. as indicated. Following brief centrifugation, 30-40 µl of pre-washed 50% Protein-A Sepharose Fast Flow beads (Sigma #9424) was added to each tube and rotated at 4° C. for 1 h at RT or 4° C. Following brief centrifugation, the supernatant was removed and the pellet washed with 500 µl of cell lysis buffer. Following three such washes, beads were used for enzymatic assays or the protein eluted by boiling the beads in 3× SDS protein loading buffer for 5 min and resolved on SDS-PAGE gels.

Phosphatase Assays

Purified human PP2Ac and rabbit PP1 were diluted to 0.01 U/µl with the dilution buffer provided and stored in aliquots at −20° C.

Phosphopeptide Assays with Purified Phosphatases 1 mg of synthetic phosphopeptides K-R-pT-I-R-R (Upstate #12-219) and R-R-A-pS-V-A (Upstate #12-220) were dissolved in 1.10-1.285 ml of dH$_2$O to prepare a 1 mM solution, then aliquoted and stored at −20° C. until use. 0.01-0.05 U of purified PP2A A-C dimer purified from human red blood cells, or 0.05 U of rabbit PP1 purified from skeletal muscle was mixed with 500 µM of phosphopeptide and incubated in the presence of various treatments as indicated at 37° C. on a heating block for 15 min. Each reaction was made up to a total volume of 25 µl with pNPP buffer (50 mM Tris-HCl, pH 7.0, 100 µM CaCl$_2$). The enzyme reaction was terminated by adding 100 µl of malachite green solution (0.034% malachite green in 10 mM ammonium molybdate, 1 N HCl, 3.4% ethanol, 0.01% Tween-20). Malachite green forms a stable green complex in the presence of molybdate and orthophosphate, allowing the amount of inorganic phosphate present to be measured. Absorbance was read in duplicate for each sample at 590 nm.

PP2A Immunoprecipitation and Phosphatase Assay

1×10$^6$ PC3 cells were plated in 60 mm plates and allowed attach for 8 h, then serum starved over night. Following various treatments as indicated, the media was aspirated and cells washed once with TBS. Cells were lysed in 0.3 ml of lysis buffer (20 mM Tris-HCl, pH 7.0, 1% Igepal-CA, 2 mM EDTA, 2 mM EGTA, 1× Complete Protease Inhibitor Cocktail) and phosphates removed by passing the lysate through a 2 ml Zeba Desalt Spin Column (Pierce #89890). Protein concentration of the desalted lysate was determined by the BCA assay as previously described. 100-150 µg of total protein was immunoprecipitated with 4 µg of anti-PP2A monoclonal antibody and 30 µl of Protein A-sepharose slurry at 4° C. for 2 h. Samples were then pelleted at 14,000 rpm for 1 min, washed three times in excess TBS and once with pNPP assay buffer. After the final spin all of the supernatant was carefully removed and 500 µM of phosphor-threonine peptide in a final volume of 80 µl added to the beads. Samples were incubated at 30° C. for 10 min with agitation, and the reaction terminated by the addition of malachite green solution. Absorbance was read at 590 nm for each sample in duplicate.

pNPP Hydrolysis Assay

Para-nitrophennylphosphate (PNPP) is a chemical substrate of phosphatase enzymes, which following hydrolysis of the phosphate moiety generates para-nitrophenol, an intensely yellow chromogen, soluble under alkaline conditions. In assays measuring relative phosphatase activity, 0.05 U of purified PP2A was mixed with 5 µl of 40 mM NiCl$_2$ and 5 µl of BSA solution (5 mg/ml) in a microcentrifuge tube. Various treatments were added as indicated, and the volume adjusted to 80 µl with pNPP assay buffer. Samples were pre-incubated at 37° C. for 15 min. pNPP substrate was freshly prepared before each assay by dissolving 1.5 mg/ml pNPP in 50 mM Tris-HCl, pH 7.0. To start the phosphatase reaction, 120 µl of pNPP substrate was added, and samples incubated for a further 15 min at 37° C. Absorbance of each sample was measured in duplicate at 405 nm with 590 nm as a reference. PP2A activity was calculated using the following equation: activity=(Sample volume in liters)×A$_{405}$/1.78× 10$^4$M$^{-1}$cm$^{-1}$ (Extinction coefficient)×0.25 cm×15 min×0.05 U enzyme.

Measurement of Total Free Sulfhydryl Groups

The change in free sulfhydryl groups in purified PP2A following various treatments was determined using Ellman's Reagent. To 0.01 U of PP2A was added to 37.5 µl of dilution buffer (30 mM Tris-HCl, 3 mM EDTA, pH 8.2), 12.5 µl DTNB reagent (Ellman's reagent) and 200 µl of methanol. Samples were incubated for 5 min at RT, and then extinction measured in duplicate for each at 412 nm. Results were compared to a standard curve generated with N-acetylcysteine.

Akt Kinase Activity Assay

The effect of sodium selenate on recombinant human Akt1 kinase activity was determined using the K-LISA™ AKT Activity Kit (Calbiochem #CBA019). This is an ELISA based assay that utilizes a biotinylated peptide substrate (GR-PRTSSFAEG) that is phosphorylated on the second serine by Akt1, Akt2, Akt3, SGK (Serum Glucocorticoid Kinase), and MSK1. Biotinylated Akt substrate and Akt sample are incubated in the presence of ATP in wells of Streptavidin-coated 96-well play, which allows for phosphorylation and substrate capture in a single step. The phosphorylated substrate is detected with a phospho-serine detection antibody, followed by the HRP-antibody conjugate, and colour development with TMB substrate.

At the start of each assay run, a new aliquot of biotinylated Akt substrate working solution was prepared by diluting the stock solution 1:100 with dH$_2$O. The following was then added to each well in this order: 10 µl of 5× Kinase Assay Buffer; 10 µl of Biotinylated Akt Substrate working solution; 250 ng of recombinant human Akt1 in 10 µl of dH$_2$O; 500 µM sodium selenate or 1 µM staurosporine in 10 µl of dH$_2$O, or just dH$_2$O for positive controls; 10 µl of 5× ATP/MgCl$_2$ mix to a total of 50 µl per well. The plate was sealed with plate-sealer, mixed briefly on a microplate shaker, and incubated for 30 m at 30° C. The kinase reaction was then stopped by adding 10 µl of kinase stop solution to each well. The contents of each well was discarded, and then washed 3 times with 1× ELISA wash solution (prepared by diluting the stock ELISA was solution 1:20 with dH$_2$O), inverted and tapped on blotting paper until dry. 100 µl of phospho-serine detection antibody working solution (prepared freshly for each assay run by diluting the phospho-serine antibody stock 1:1000 with dH$_2$O) was then added to each well and incubated for 1 h at RT. The plate was then washed as described above. 100 µl of HRP-antibody conjugate working solution (prepared freshly for each assay run by diluting the HRP-antibody stock 1:1000 with dH$_2$O) was then added to each well at incubated for 1 h at RT. The plate was then washed again as described above. 100 µl of TMB substrate was then added to each well, and the colour allowed to develop for 20 min at RT. The reaction was halted by adding 100 µl of ELISA stop solution to each well, and absorbance read at 450 nm with reference to 590 nm using a microplate reader.

Intracellular Redox State Assay

Intracellular redox state was determined using 2',7'-dichlorodihydrofluorescein diacetate (DCFDA). DCFDA is non-fluorescent and freely cell permeable, but in the presence of reactive oxygen species (ROS) is rapidly converted to the cell impermeable but highly fluorescent 2',7'-dichlorofluorescein (DCF). Cells were equilibrated with 5 µM of DCFDA for 15 min prior to various treatments. Adherent cells were then harvested, washed twice with PBS and the proportion of fluorescent cells determined immediately by flow cytometry.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

Example 10

Effects of Selenate on Tau Phosphorylation Activities Both on Mouse Brain Tissues and Human Neuroblastoma Cell Lines Materials and Methods Cell Culture. Human neuroblastoma SY5Y and BE2M17 cell lines were obtained from Janetta Culvenor (Department of Pathology, University of Melbourne, VIC). SY5Y cells were routinely cultured in RPMI 1640 medium (Invitrogen, Auckland, New Zealand) supplemented with 10% fetal bovine serum (FBS, Invitrogen, GIBCO), 1% non-essential amino acids (Sigma, St Louis, Mo., USA), 10 mM HEPES (Invitrogen, GIBCO), 1 mM sodium pyruvate (Invitrogen, GIBCO) and 1% antibiotic/antimycotic mixture (Invitrogen, GIBCO). BE2M17 cells were cultured in OPTI-MEM I reduced serum medium (Invitrogen, GIBCO) supplemented with 10% FBS (Invitrogen, GIBCO), 1% non-essential amino acids (Sigma, St Louis, Mo., USA), 1 mM sodium pyruvate (Invitrogen, GIBCO), and 1% antibiotic/ antimycotic mixture (Invitrogen, GIBCO). Cells were cultured at 37° C. in 5% $CO_2$. Sodium selenate was obtained from Sigma (St Louis, Mo., USA).

Antibodies: The following antibodies were obtained from Pierce Endogen (Rockford, USA) unless otherwise stated: anti-human PHF-Tau monoclonal (clone AT100; AT180; AT270), and anti-human Tau monoclonal (clone HT-7). Polyclonal goat anti-mouse immunoglobulins/HRP (Dako, Denmark) and Anti-tubulin (G712A, Promega).

In Vitro: $2 \times 10^5$ SY5Y or BE2M17 cells were plated to each well in a Falcon 6-well plate, either over coated or uncoated surfaces, and were allowed to attached overnight at 5% $CO_2$/37° C. in complete growth medium (as described above). The medium was replaced with fresh complete growth medium containing 100 µM concentration of sodium selenate and were cultured for 3 hours. Cells were cultured over Falcon 6-well plates with surfaces coated either with 0.1% gelatin (Sigma, St Louis, Mo., USA), matrigel (cat #354234, BD, NSW, Australia) or 0.5 µg/ml fibronectin (Sigma, St Louis, Mo., USA).

In Vivo: 14 weeks old Balb/C Nu Nu male mice were obtained from ARC. Mice receive a single subcutaneous injection of 300 µg sodium selenate per 200 µl in PBS. Mice were sacrificed at various time points following injection and blood and brain tissues specimen were collected.

Lysates preparation and Immunoblotting: Cells were washed twice in cold PBS and were lysed in 150 µl of cold RIPA buffer (containing 10% glycerol, 20 mM Tris, 137 mM NaCl, 0.1% SDS, 0.05% IGEPAL, 1% Triton X-100, 2 mM EDTA, 10% NaV, 2% NaF and 4× protease inhibitor), similarly, brain tissues were homogenised in dry ice using mortar and pestle, and lysed in 150 µl RIPA buffer. Samples were incubated on ice for 30 minutes, followed by centrifugation at 13000 rpm/ 10 minutes/ 4° C. Supernantant was collected and protein estimation was calculated for each sample by using BCA reagent (Sigma). Equal amounts of protein were loaded into each lane of a 10% SDS-polyacrylamide gel. The proteins were transferred onto PVDF (Millipore) membranes and were blocked with 5% skim milk blotto for 2 hours. After blocking the membrane, primary antibodies: either anti-human PHF-Tau (AT100 at 1:200, AT180 at 1:1000, and AT270 at 1:2500) or anti-human Tau (HT-7 at 1:1000) were incubated overnight at 4° C. in 5% skim milk blotto. Prior to secondary antibody incubation, membranes were rinsed 3× followed by 3×5 minutes washed in Tris-Buffered Saline with 0.01% Tween at room temperature. Followed by 1 hour incubation of secondary antibody polyclonal goat anti-mouse (Dako, Denmark) coupled to horse radish peroxidase (HRP) at 1:10000 dilutions in 5% skim milk blotto/room temperature. Membranes were washed as described above and were detected by using Amersham ECL western blotting detection reagent (Amersham Bioscience, Buckinghamshire, UK). Membranes were stripped using 2% SDS/β-Mercaptoethanol stripping buffer and reprobed for tubulin (Promega) to confirm protein loading.

Figure 11:
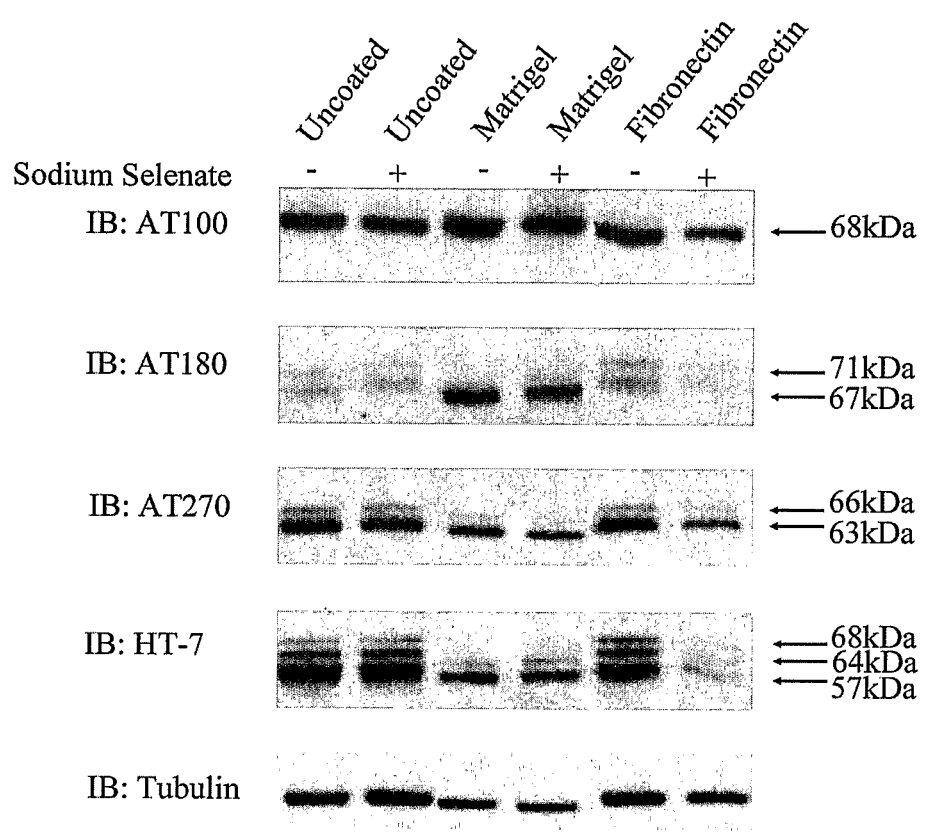
FIG. 11 is a comparative representation of immunoblotting of human neuroblastoma BE2M17 cell line with anti-human PHF-tau antibodies in the presence (+) or absence (−) of sodium selenate under various coating conditions.

Immunoblotting of human neuroblastoma BE2M17 cell line with anti-human PHF-Tau in the presence (+) or absence (−) of sodium selenate, under various coating surfaces is shown in FIG. 11. Sodium selenate at 100 µM was prepared in BE2M17 complete growth medium. Cells were cultured with sodium selenate for 3 hours on fibronectin, uncoated (plastic) or matrigel (as described in methods section).

Results:

Anti-human PHF-Tau clone AT100 was detected at 68 kDa. In the presence of sodium selenate, PHF-Tau signal appeared to be reduced from cells cultured on fibronectin, and matrigel, in comparison to non-selenate treated cells.

Anti-human PHF-Tau clone AT180 was detected both at 71 and 67 kDa. Selenate treated cells cultured on fibronectin, plastic (uncoated) and matrigel appeared to have a weaker PHF-Tau signal compared to non-selenate treated cells. Cells cultured on matrigel give a stronger signal of PHF-Tau at 67 kDa compared to cells cultured on fibronectin and plastic.

Anti-human PHF-Tau clone AT270 was detected both at 66 and 63 kDa. Selenate treated cells cultured on fibronectin, plastic (uncoated) and matrigel appeared to have a weaker PHF-Tau signal compared to non-selenate treated cells. Note, there is only a slight difference between selenate treated and non-treated cells cultured on matrigel.

Anti-human Tau clone HT-7 was detected at 68, 64, and 57 kDa. Cells cultured on fibronectin with selenate appeared to reduce Tau expression.

Anti-tubulin was detected showing equal protein loading.

Figure 12:
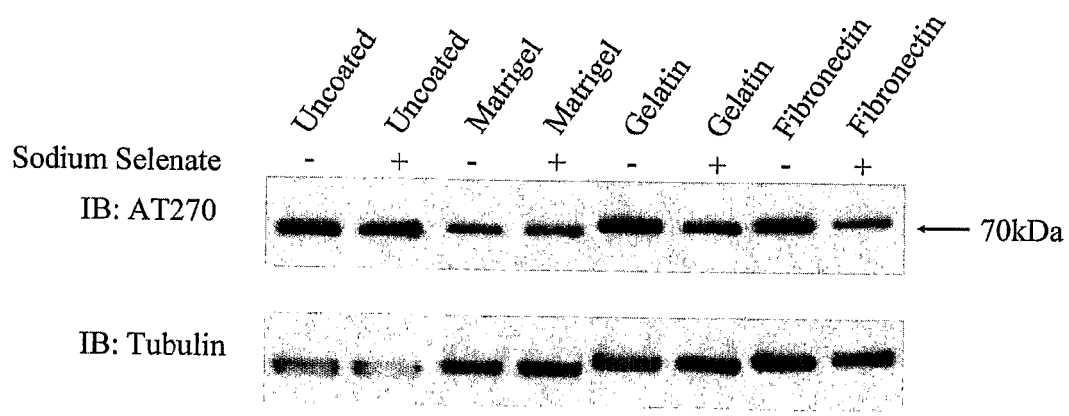
FIG. 12 is a comparative representation of immunoblotting of human neuroblastoma SY5Y cell lines with anti-human PHF-tau antibodies, AT270 (FIG. 12A) and HT-7 (FIG. 12B), in the presence (+) or absence (−) of sodium selenate under various coating conditions.
Figure 12:
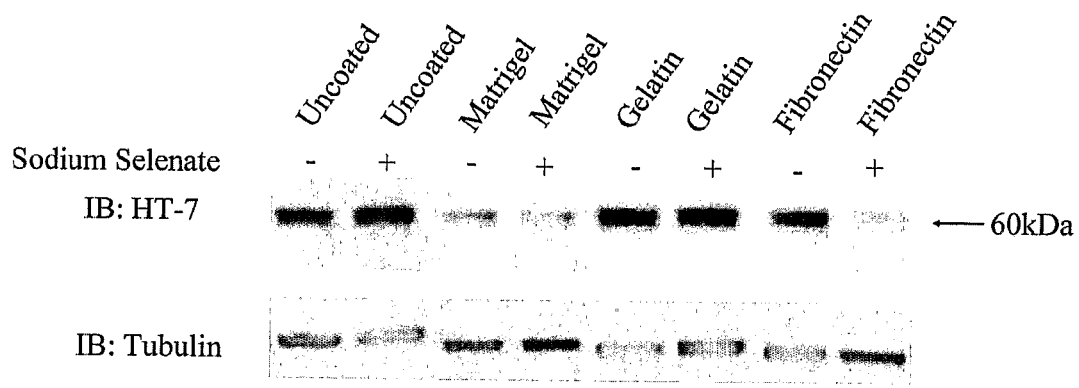

Immunoblotting of human neuroblastoma SY5Y cell lines with anti-human PHF-Tau in the presence (+) or absence (−) of sodium selenate, under various culturing surfaces is shown in FIG. 12. Sodium selenate at 100 µM was prepared in SY5Y complete growth medium. Cells were cultured with sodium selenate for 3 hours on gelatin, fibronectin, uncoated (plastic) or matrigel (as described in methods section).

Results:

Anti-human PHF-Tau clone AT270 specifically detected at 70 kDa. Selenate treated cells cultured on gelatin and fibronectin appeared to have a weaker PHF-Tau signal compared to non-selenate treated cells.

Anti-human Tau clone HT-7 was detected at 60 kDa. Both matrigel and fibronectin appeared to reduced anti-Tau signal. In particularly, cells cultured on fibronectin with selenate appeared to have a weaker signal for anti-Tau than those cultured without selenate.

Anti-tubulin was detected showing relative equal protein loading.

Figure 13:
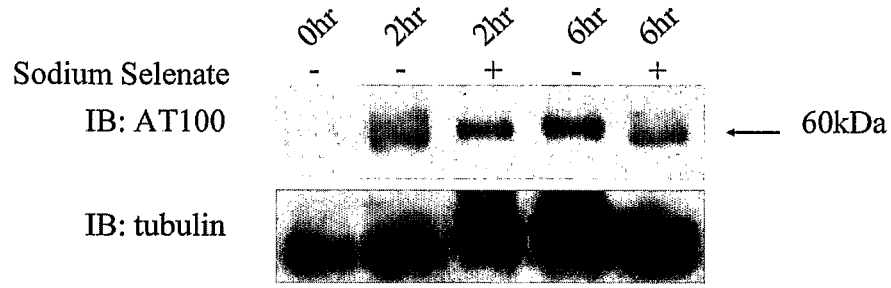
FIG. 13 is a comparative representation of immunoblotting of total brain lysates from 14 weeks old Balb/c Nu Nu male mice with anti-human PHF-tau antibodies, AT100 (FIG. 13A), AT180 (FIG. 13B), AT270 (FIG. 13C) and HT-7 (FIG. 13D), in the presence (+) or absence (−) of sodium selenate.
Figure 13:
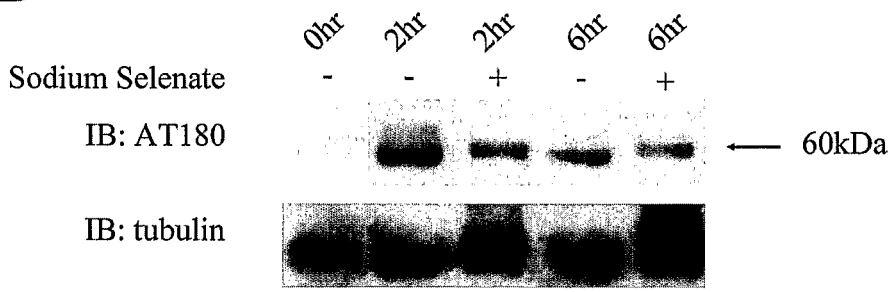
Figure 13:
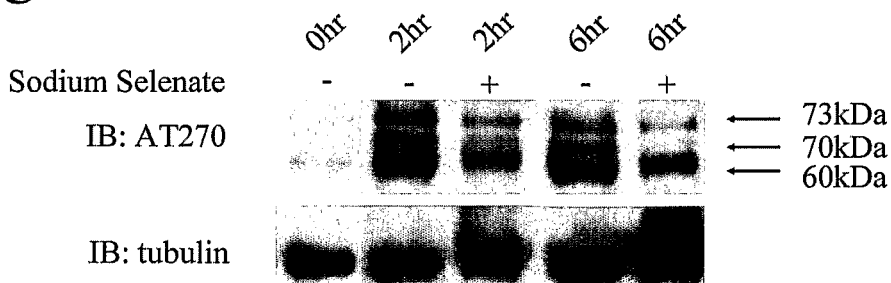
Figure 13:
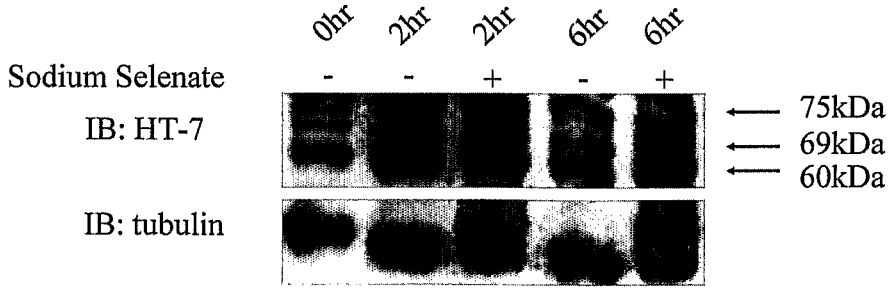

Immunoblotting of total brain lysates from 14 weeks old Balb/C Nu Nu male mice with anti-human PHF-Tau (as indicated) either with (+) or without (−) sodium selenate is shown in FIG. 13. Mice treated with sodium selenate were given by subcutaneous injection at 1.5 µg/µl. In the absence of sodium selenate (−) mice were subcutaneously injected with PBS.

Brain tissue was collected at various time points: 0, 2, and 6 hours (as described in methods section).
Results:
PBS appeared to have an effect on anti-human PHF Tau signal for all clones studied (AT100, AT180 and AT270). To confirm equal protein loading all membranes were stripped and reprobed for tubulin as described in the methods section.

FIG. 13A shows the immunoreactivity of anti-human PHF Tau clone AT100 at 60 kDa. In the presence of sodium selenate, PHF Tau signal appeared to be reduced at 2 and 6 hours time point compared to selenate non-treated cells.

FIG. 13B shows immunoreactivity of anti-human PHF Tau clone AT180 at 60 kDa. In the presence of sodium selenate, PHF Tau signal clearly reduced at 2 and 6 hours compared to selenate non-treated cells.

FIG. 13C shows similar immunoreactivity signals of AT270 compared to AT180 clones. It appeared that AT270 clones detected three isoforms of PHF Tau at 73, 70 and 60 kDa.

FIG. 13D shows the expression of Tau protein in mice brain total lysates either with (+) or without (−) sodium selenate. Anti-human Tau, specifically clone HT-7 in mice brain tissues appeared to be non-specific.

Example 11

Effects of Sodium Selenate on Behaviour and Tau Brain Pathology of Transgenic Mice Over-expressing Human Tau 441 (TMHT)

Methods
Introduction

The study was designed to evaluate the effects of a treatment with sodium selenate on behaviour and brain morphology of TAU441 transgenic (Tg) TMHT mice (C57BL6 background) over-expressing the human TAU441 gene with two mutations, V337M and R406W, under the control of a brain specific murine Thy-1 promoter. Behaviour of all Tg mice was evaluated after 1.5 and 3 months after treatment in the Open Field (OF) test, the Rota Rod (RR) test and the Nose poke curiosity and activity test, the latter to evaluate curiosity behaviour. At the end of the treatment additionally memory and learning were evaluated in the Morris Water Maze (MWM) task. Untreated mice of the baseline group were also tested in the OF test, the RR test, the Nose poke test and the MWM task. Brain TAU pathology, were determined initially in 3 animals per treatment group.

Animals

Male and female Tg TMHT mice expressing human TAU441 bearing the missense mutations V337M and R406W under the regulatory control of the brain specific murine Thy-1 promoter were used. Mice were generated and bred at JSW-Research, Graz, Austria. The C57BL/6 background for these mice result in the mice being known as good learners. This mouse model resembles human Alzheimer's disease tau-pathology. At treatment start mice had an age of 5 months±2 weeks and this was also the age of the baseline group.

Animal Identification and Housing

Mice were identified with ear markings. They were housed in individual ventilated cages (IVCs) on standardized rodent bedding supplied by ABEDD®. Each cage contained a maximum of five mice. Mice were kept according to the standard operating procedures based on international standards.

Each cage was identified by a colored card indicating the study number, sex, the individual registration numbers (IRN) of the animals, date of birth, as well as the screening date and the treatment group allocation.

The temperature during the study was maintained at approximately 24° C. and the relative humidity was maintained at approximately 40-70%. Animals were housed under a constant light-cycle (12 hours light/dark).

Dried, pelleted standard rodent chow (Altromin®) and normal tap water were available to the animals ad libitum.

Treatment

Mice were randomly allocated to the groups A (sodium selenate), B (vehicle) and C (baseline). Treatment group A received sodium selenate via drinking water for 12 weeks while control mice (B) had access to normal tap water. For application, 1.2 mg sodium selenate was dissolved in 100 mL of sterile water, the weight was recorded and the bottle was placed in the cage. This was done every Monday, Wednesday and Friday, and the water was weighed on exchange to measure consumption.

Behavioural Testing
Open Field Test

The most standardized general measure of locomotor function is spontaneous activity in the Open Field (OF). For the present investigations, a Plexiglas Open Field (48×48 cm; TSE-System®) was used. The infrared photo beams were placed at 1.4 cm distance around the box. To detect rearing (standing on the hind paws) another row of photo beams was mounted 4 cm above the first one. The test session lasted for 5 minutes to check the mouse behaviour in the new surroundings as well as habituation. Thereafter the number of fecal boluses was counted, as a measure of emotionality. The OF was cleaned with 70% ethanol after every mouse to remove odour traces. Testing was performed under standard room lighting conditions during the light phase of the circadian cycle.

Rota Rod Test

This test was used to detect possible motor deficits of the TAU Tg mice. Investigations were conducted on an accelerating five-lane-Rota Rod (TSE-Systems®). The mice had to complete a program for maximal 300 sec. They started with a speed of 5 rpm and after 120 sec the rod reached a speed of 60 rpm. After this run, the latency to fall and the speed of the rod at that time were calculated.

Nose Poke Curiosity and Activity Test

The hole-board apparatus offers a simple method of measuring the responses of a mouse to a novel environment and takes advantage of the curious nature of mice and their tendency to poke their noses into holes. The investigation of curiosity behaviour was done in OF boxes equipped with hole-boards (16 holes/board). Head dipping into a hole interrupted the infrared beams just below the edge of each hole. Number and duration of the head dippings were calculated for each animal during a 5-minute period.

Morris Water Maze (MWM)

The Morris Water Maze task was conducted in a black circular pool of a diameter of 100 cm. The pool was filled with tap water at a temperature of 22±1° C. and the pool was virtually divided into four sectors. A transparent platform (8 cm diameter) was placed about 0.5 cm beneath the water surface. During the whole test session, except the pretest, the platform was located in the southwest quadrant of the pool.

One day before the 4 days lasting training session animals had to perform a so called "pre-test" (two 60 second trials) to ensure that the visual ability of each animal were normal. Only animals that fulfilled this task continued to the MWM testing.

In the MWM task each mouse had to perform three trials on four consecutive days. A single trial lasted for a maximum of one minute. During this time, the mouse had the chance to find the hidden, diaphanous target. If the animal could not find a "way" out of the water, the investigator guided to or placed the mouse on the platform. After each trial the mouse was allowed to rest on the platform for 10-15 seconds. During this time, the mouse had the possibility to orientate in the surroundings. Investigations took place under dimmed light conditions, to prevent the tracking system from negative influences (Kaminski; PCS, Biomedical Research Systems). On the walls surrounding the pool, posters with black, bold geometric symbols (e.g. a circle and a square) were fixed which the mice could use the symbols as landmarks for orientation.

One swimming group per trial consisted of five to six mice, so that an intertrial time of about five to ten minutes was ensured.

For the quantification of escape latency (the time in seconds the mouse needed to find the hidden platform and therefore to escape from the water), of pathway (the length of the trajectory in meters to reach the target) and of the abidance in the goal quadrant a computerized tracking system was used. The computer was connected to a camera placed above the centre of the pool. The camera detected the signal of the light emitting diode (LED), which was fixed with a little hairgrip on the mouse's tail.

Probe Trial

One hour after the last trial on day 4, mice had to fulfill a so-called probe trial. At this time, the platform was removed from the pool and during the one-minute probe trial, the experimenter counted the number of crossings over the former target position. Additionally the abidance in this quadrant was measured.

Tissue Preparation and Sampling

At the end of the treatment period, and following all behavioural testing, at sacrifice from each animal, blood (plasma and serum), CSF and brain were obtained, processed immediately or stored for further experiments.

For that purpose all mice were sedated by standard inhalation anesthesia (Isofluran, Baxter). Cerebrospinal fluid was obtained by blunt dissection and exposure of the foramen magnum. Upon exposure, a Pasteur pipette was inserted to the approximate depth of 0.3-1 mm into the foramen magnum. CSF was collected by suctioning and capillary action until flow fully ceased. Each sample was immediately frozen and kept at −80° C. until ready for further analysis with ELISA technique.

After CSF sampling, each mouse was placed in dorsal recumbence and a 26-gauge needle attached to a 1 mL syringe was inserted into the thorax through the diaphragm to an approximate depth of 2 cm. Light suction was applied to the needle and placement in the cardiac (ventricular) chamber of the mouse was confirmed by blood flow to the syringe chamber. Blood was aspirated until flow ceased, collected in EDTA vials and stored at −20° C. until later use.

After blood sampling transgenic mice were intracardially perfused with 0.9% sodium chloride. Brains were rapidly removed, and the right half was immersion fixed for 24 hours in freshly prepared 4% Paraformaldehyde and embedded in paraffin for histological investigations. The left hemisphere was frozen on dry ice and stored at −80° C. for possible later biochemical analysis.

In initially nine (9) brain hemispheres (≥3 per Tg animal group) histological evaluations were performed to qualitative and quantitative evaluate TAU pathology.

Fifteen (15) coronal consecutive sections (Leica SM 2000R) were cut (5 μm thick) at each of 5 different brain layers between Bregma −1.82 and −1.34 mm, which were chosen according to the morphology atlas "The Mouse Brain" from Paxinos and Franklin ($2^d$ edition), for Gallyas staining and for determination TAU pathology with specific antibodies (AT180 and HT7). Tissues of all transgenic animals investigated were handled in exactly the same way to avoid bias due to variation of this procedure. Remaining brain hemispheres or tissue not used are saved and stored until the sponsor has decided to how to proceed or until end of the study.

Immunohistochemical Determination of TAU Pathology

TAU depositions were determined using the monoclonal TAU-antibodies AT180 and HT7 (Pierce Endogen®). AT180 recognizes PHF-TAU and tangle like formations [the epitope of this antibody is the phosphorylated Thr231 residue] and HT7 normal human TAU and PHF-TAU [the epitope of this antibody has been mapped on human TAU between residue 159 and 163].

Five (5) μm thick coronal paraffin sections from each of the five different layers were stained with the above described monoclonal mouse anti-human TAU-antibodies (AT180—1:100; HT7—1:1000) and visualized using a secondary anti-mouse Cy3 (1:500, Jackson Laboratories®). The detailed staining protocols are set out below:

AT180 incubation protocol for the determination of human PHF-TAU depositions

1.) Deparaffinize and hydrate tissue sections through Tissue Clear (Sakura®) and graded alcohol (Merck®) series.
2.) Wash for 2 minutes in Aqua bidest (Fresenius-Kabi®)
3.) Place tissue sections for antigen unmasking in 10% citrate buffer (Labvision®) for 15 minutes at 95° C. in a steamer and to cool down for 15 minutes at room temperature.
4.) Wash sections for 2×5 minutes in PBS.
5.) Block endogenous peroxidase with 1% hydrogen peroxide (Linaris®) in methanol (Merck®) for 10 minutes at room temperature.
6.) Wash sections for 2×5 minutes in PBS.
7.) Block unspecific bindings with MOM-Blocking Reagent (Vector®) for 60 minutes at room temperature in a damp chamber.
8.) Wash sections for 2×5 minutes in PBS.
9.) Block unspecific bindings with MOM-Diluent (Vector®) for 5 minutes at room temperature.
10.) Incubate with AT180 (Pierce Endogen®; 1:100 in MOM-Diluent) for 60 minutes at room temperature in a damp chamber.
11.) Wash sections for 3×5 minutes in PBS.
12.) Block unspecific bindings with 10% Non-Immune Goat-Normal Serum (Dako®) for 10 minutes at room temperature in a damp chamber.
13.) Wash sections for 2×5 minutes in PBS.
14.) Incubate with Cy 3 Goat Anti-Mouse (Jackson®; 1:500 in MOM-Diluent) for 60 minutes at room temperature in a damp chamber.
15.) Wash sections for 5 minutes in PBS.
16.) Wash sections for 5 minutes in Aqua bidest.
17.) Cover sections with Moviol and coverslips.

Chemicals and Reagents:

1% hydrogen peroxide in methanol:
60 mL methanol+2 mL 30% hydrogen peroxide+0.6 mL Triton X-100 (Amresco®).

MOM-Blocking Reagent:
2 drops of MOM-Mouse IgG Blocking Reagent (from MOM-Kit (Vector®))+2.5 mL PBS.

MOM-Diluent:
10 mL PBS+800 μL Protein Concentrate (from MOM-Kit (Vector®)).

Antibody AT180:
  1:100 in MOM-Diluent
Antibody Cy3 Goat Anti-Mouse:
  1:500 in MOM-Diluent
HT7 incubation protocol for the determination of normal human TAU and PHF-TAU depositions
  1.) Deparaffinize and hydrate tissue sections through Tissue Clear (Sakura®) and graded alcohol (Merck®) series.
  2.) Wash for 2 minutes in Aqua bidest (Fresenius-Kabi®).
  3.) Place tissue sections for antigen unmasking in 1% citrate buffer (Labvision®) for 15 minutes at 95° C. in a steamer and to cool down for 15 minutes at room temperature.
  4.) Wash sections for 2×5 minutes in PBS.
  5.) Block endogenous peroxidase with 1% hydrogen peroxide (Linaris®) in methanol (Merck@) for 10 minutes at room temperature.
  6.) Wash sections for 2×5 minutes in PBS.
  7.) Block unspecific bindings with MOM-Blocking Reagent (Vector®) for 60 minutes at room temperature in a damp chamber.
  8.) Wash sections for 2×5 minutes in PBS.
  9.) Block unspecific bindings with MOM-Diluent (Vector®) for 5 minutes at room temperature.
  10.) Incubate with HT7 (Pierce Endogen®; 1:1000 in MOM-Diluent) for 60 minutes at room temperature in a damp chamber.
  11.) Wash sections for 3×5 minutes in PBS.
  12.) Block unspecific bindings with 10% Non-Immune Goat-Normal Serum (Dako®) for 10 minutes at room temperature in a damp chamber.
  13.) Wash sections for 2×5 minutes in PBS.
  14.) Incubate with Cy 3 Goat Anti-Mouse (Jackson®; 1:500 in MOM-Diluent) for 60 minutes at room temperature in a damp chamber.
  15.) Wash sections for 5 minutes in PBS.
  16.) Wash sections for 5 minutes in Aqua bidest.
  17.) Cover sections with Moviol and coverslips.
Chemicals and Reagents:
  1% hydrogen peroxide in methanol:
  60 mL methanol+2 mL 30% hydrogen peroxide+0.6 mL Triton X-100 (Amresco®).
  MOM-Blocking Reagent:
  2 drops of MOM-Mouse IgG Blocking Reagent (from MOM-Kit (Vector®))+2.5 mL PBS.
  MOM-Diluent:
  10 mL PBS+800 µl Protein Concentrate (from MOM-Kit (Vector®)).
  Antibody HT7:
  1:1000 in MOM-Diluent
  Antibody Cy3 Goat Anti-Mouse:
  1:500 in MOM-Diluent
  Evaluation
  Behaviour In the Open Field (OF) the horizontal and vertical activity, number of fecal boli, number and duration of rearing, hyperactivity and time spent in the centre versus time spent in the perimeter of the open field were measured.

In the Nose poke curiosity and activity test the number and duration of the head dippings was calculated.

In the Rota Rod test the latency to fall and the speed of the rod at that time were calculated.

In the Morris water maze trials length of swimming path and escape latencies were recorded. Swimming speed was calculated as swimming path divided by escape latency. In the probe trial, a trial with removed platform, the number of crossings over the former platform position was recorded to the data sheet as well as the time spent in each quadrant of the pool.

Neuropathlogy

To determine the extent of TAU immunoreactivity in hippocampus and amygdala specialized image analysis software (Image Pro Plus, version 4.5.1.29) was used. Following parameters were evaluated and calculated:
  region area of hippocampus and amygdala in each slice
  absolute area of immunoreactive positive cells in the specific brain regions hippocampus and amygdala
  number of immunoreactive positive area relative to the specific brain region area of the hippocampus and amygdala Quantification procedure:
  a) Contrasting the image for better visualization of slice morphology without applying the contrast to the image.
  b) Interactive drawing of the hippocampal outlines and measurement of the hippocampal area (=region area).
  c) Interactive drawing of the area of interest (AOI), in which stained objects are detected over an intensity based threshold level. To determine the threshold value a line histogram was interactively drawn close to the AOI in an area without visible immunoreaction. The mean intensity level from all pixels of the line histogram plus a constant defined the intensity threshold level. Objects below a size of 7 $\mu m^2$ were excluded.
  d) Measurement of the area of each object and the sum of stained area in the AOI.
  e) Repetition of a-d) for the amygdala.
  f) Calculation of the relative TAU immunopositive area (="sum area of TAU immunoreactivity/region area*100").
  g) Automated data export into an Excel spread sheet, including the parameters "image title, region area, total TAU area and TAU area in percentage. A field for remarks was used to record image quality and exclusion criteria, respectively. Exclusion criteria were missing parts of the slice, many wrinkles or dominant flaws.
  h) Closing the image without saving (to keep raw data).

Statistics

Means, standard deviation or SEMs were calculated for all measured parameters.

Results

General Observations

In general it can be stated that the treatment with sodium selenate did not lead to any negative side effects or caused any premature deaths.

Behavioural Results

Open Field

Figure 14:
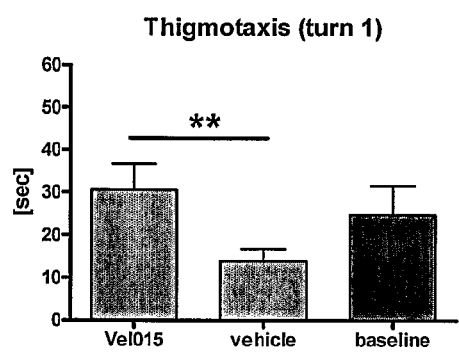
FIG. 14 graphically represents the effects of treatment with sodium selenate on behaviour tested in the Open Field (thigmotaxis) at turn 1 (FIG. 14A) and at turn 2 (FIG. 14B).
Figure 14:
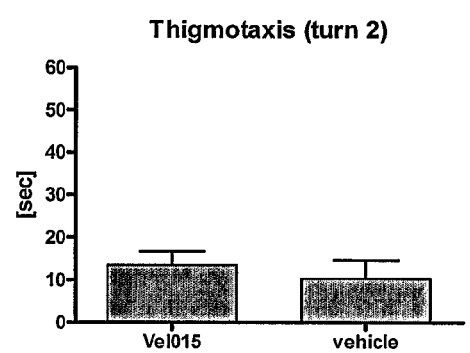

While activity parameters (activity, hyperactivity, rearing behaviour) were uninfluenced by sodium selenate treatment, sodium selenate treated mice showed disturbed thigmotactic behaviour during the first OF session. This resulted in a significant higher abidance in the centre of the Open Field box, meaning less thigmotaxis, between vehicle and sodium selenate treated animals in the first turn (see FIG. 14—"thigmotaxis", T-test for treated animals: $p=0.019$). At the end of treatment in turn 2 thigmotactic behaviour normalized to the level of the vehicle controls.

Baseline animals featured higher defecation rates in the OF test versus both treated groups investigated one and a half months later (ANOVA: $p=0.018$, $p<0.05$ for both treated groups) indicating a higher emotional reaction to the test procedure.

Rota Rod

Motor performance remained unchanged with sodium selenate treatment.

Nose Poke Curiosity and Activity Test

Curiosity behaviour remained unchanged with sodium selenate treatment.

Morris Water Maze

Figure 15:
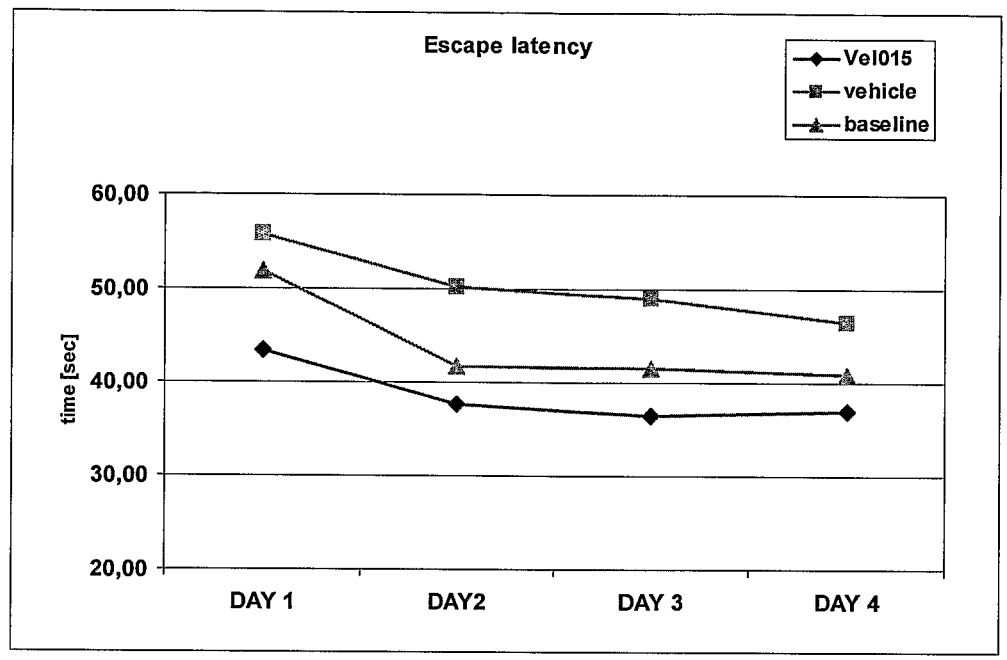
FIG. 15 graphically represents the effects of treatment with sodium selenate on learning and memory tested in the Morris Water Maze task as assessed by escape latency (time in seconds, FIG. 15A) and swimming path (length in meters, FIG. 15B).
Figure 15:
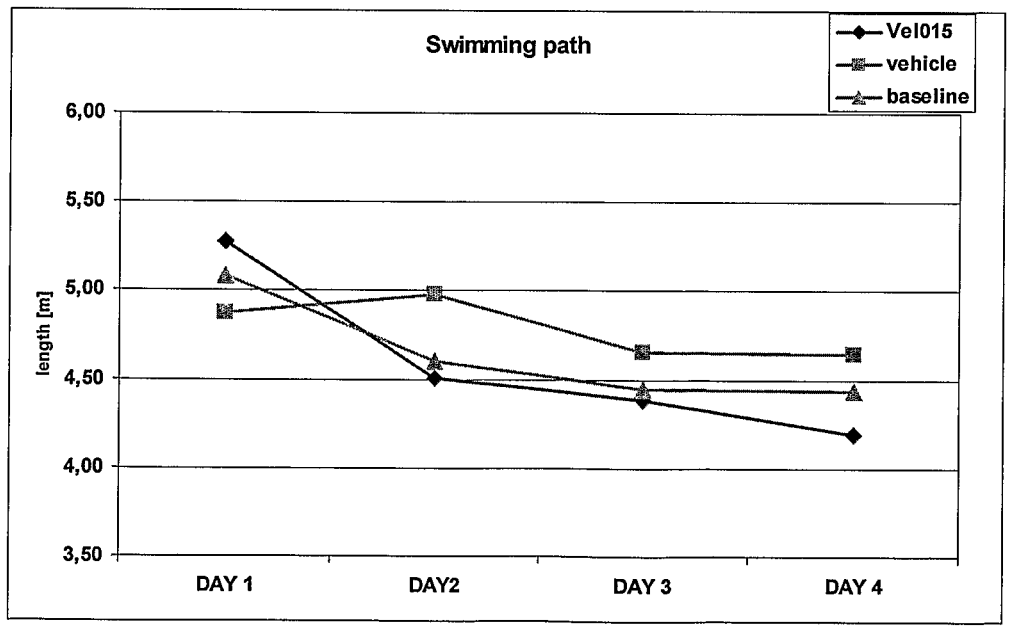

Results of the Morris Water Maze (MWM) performance of the two different treatment groups plus baseline (5 months old animals treatment) are shown in FIG. 15 and Table 4 showing the results of the statistical analysis. The MWM task revealed pronounced in some cases (see Table 4) even significant differences between sodium selenate treated animals in comparison to the vehicle group and even in comparison to the three months younger baseline group.

TABLE 4

Table of Mann Whitney U-test results for Morris Water Maze results:

| | TIME | | | LENGTH | | |
|---|---|---|---|---|---|---|
| | sel vs vehicle | | | sel vs vehicle | | |
| | n sel | n vehicle | p-values | | n sel | n vehicle | p-values |
| DAY 1 | 15 | 16 | 0.0020 | DAY 1 | 15 | 16 | 0.4945 |
| DAY 2 | 15 | 16 | 0.0082 | DAY 2 | 15 | 16 | 0.4701 |
| DAY 3 | 15 | 16 | 0.0267 | DAY 3 | 15 | 16 | 0.6823 |
| DAY 4 | 15 | 16 | 0.1015 | DAY 4 | 15 | 16 | 0.5196 |
| | sel vs baseline | | | sel vs baseline | | |
| | n sel | n baseline | p-values | | n sel | n baseline | p-values |
| DAY 1 | 15 | 15 | 0.0295 | DAY 1 | 15 | 15 | 0.6236 |
| DAY 2 | 15 | 15 | 0.6827 | DAY 2 | 15 | 15 | 0.8063 |
| DAY 3 | 15 | 15 | 0.3669 | DAY 3 | 15 | 15 | 1.0000 |
| DAY 4 | 15 | 15 | 0.5125 | DAY 4 | 15 | 15 | 0.9349 |
| | vehicle vs baseline | | | vehicle vs basline | | |
| | n vehicle | n baseline | p-values | | n vehicle | n basline | p-values |
| DAY 1 | 16 | 15 | 0.5196 | DAY 1 | 16 | 15 | 0.6260 |
| DAY 2 | 16 | 15 | 0.0655 | DAY 2 | 16 | 15 | 0.7701 |
| DAY 3 | 16 | 15 | 0.1195 | DAY 3 | 16 | 15 | 0.7112 |
| DAY 4 | 16 | 15 | 0.1751 | DAY 4 | 16 | 15 | 0.6260 |

The results clearly show the potential of sodium selenate improving cognitive functions.

Results of Brain Histology and Immunohistochemistry

General results

In the quantifications of AT180 and HT7 IHC region areas of the hippocampus and the amygdala were highly constant throughout all investigated brains, which excludes negative effects on tissue in immunohistochemical staining steps (e.g. shrinkage, different cutting circumstances), and is furthermore a sign that there was no treatment induced atrophy. Measured TAU load data were related to the individual region size in the slice to be able to cope with minimal differences.

HT7 and AT180

Figure 16:
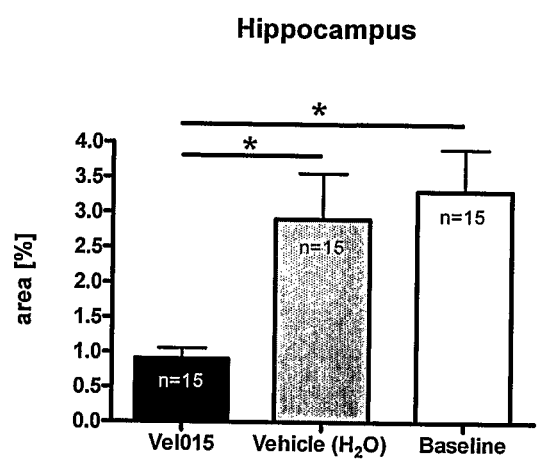
FIG. 16 graphically represents the effect of sodium selenate on Tau load in the hippocampus (FIG. 16A) and in the amygdala (FIG. 16B) as determined by HT7 Immunohistochemistry in hTAU441 transgenic TMHT mice.
Figure 16:
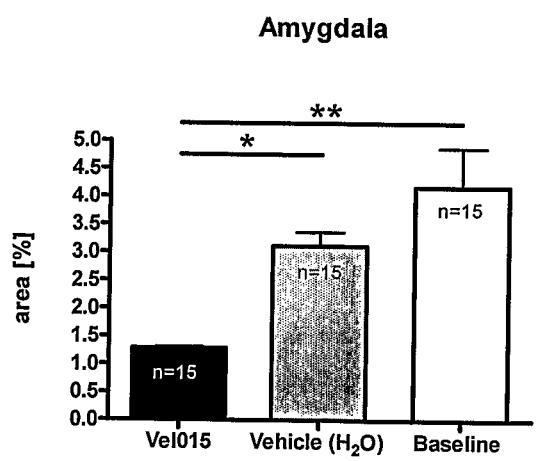

The percentage of relative HT7-TAU area in the hippocampus was significantly reduced in animals treated with sodium selenate (1.2 mg) versus vehicle (ANOVA: $p<0.05$, T-Test of treated groups: $p=0.04$) and untreated baseline groups (ANOVA: $p<0.05$; see FIG. 16A). This effect was more pronounced in the Amygdala (see FIG. 16B) in which the sodium selenate treated mice showed significantly reduced percentage of relative HT7-TAU area versus untreated baseline group (ANOVA: $p<0.01$) and versus vehicle treated animals (ANOVA: $p<0.05$; T-test for treated only: $p=0.0018$).

Figure 17:
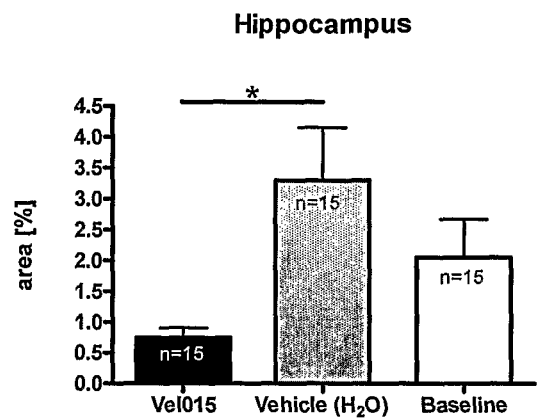
FIG. 17 graphically represents the effect of sodium selenate on Tau load in the hippocampus (FIG. 17A) and in the amygdala (FIG. 17B) as determined by AT180 immunohistochemistry in hTAU441 transgenic TMHT mice.
Figure 17:
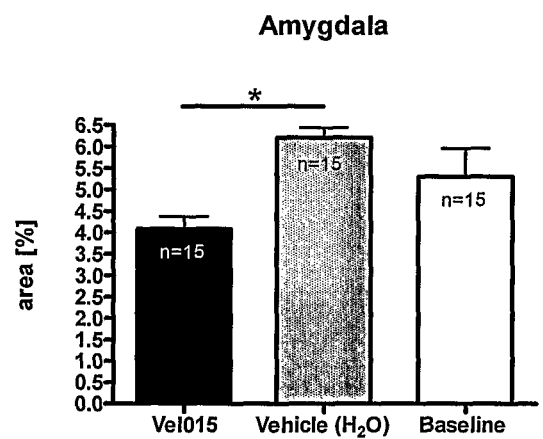

Similar to HT7-TAU also the percentage of relative AT180-TAU area in the hippocampus was reduced in animals treated with sodium selenate (1.2 mg) versus vehicle (T-Test of treated groups: $p=0.04$, see FIG. 17A), however at lower level of significance. Again this effect was more pronounced in the Amygdala (see FIG. 17B) in which the sodium selenate treated mice showed significantly reduced percentage of relative HT7-TAU area versus vehicle group (ANOVA: $p<0.05$, T-Test of treated groups: $p=0.0045$) but not versus untreated baseline group.

AT180 and HT7 immunoreactive positive neurons in hippocampus and amygdala showed massive TAU depositions in neuronal soma, which was densely packed with PHF TAU. Sodium selenate treatment visibly reduced TAU load as well as TAU positive cells in the amygdala and neuronal layer of the hippocampal CA1 region.

SUMMARY OF EFFECTS AND CONCLUSIONS

Less thigmotaxis one and a half month after treatment start hints at changes in fear related to amygdaloideic structures in the sodium selenate treated transgenic mice. After prolonged sodium selenate treatment mice returned to comparable and normal thigmotactic behavior of vehicle treated controls in the second Open Field test run before sacrificing.

All motor parameters like RotaRod performance, Open Field activity, hyperactivity and rearing behavior were uninfluenced by sodium selenate treatment.

The treatment with sodium selenate could improve cognitive abilities tested in the Morris Water Maze. On day 1, 2 and 3 sodium selenate treated animals could find the platform high significantly ($p \leq 0.01$) faster than animals from the vehicle and on day 1 also faster than the three months younger animals from the baseline group.

Pronounced effects of a treatment with sodium selenate can be seen when evaluating HT7 immunopositive TAU deposition and TAU load in hippocampus and amygdala of TMHT Tg mice.

Due to the treatment a significant reduction of HT7 positive TAU area in hippocampus and amygdala compared to the untreated baseline group or rather in the amygdala also to the vehicle ($H_2O$) treated controls can be seen.

Results on HT7-TAU deposition are supported by the AT180 incubation. Here a significant reduction of AT180 positive TAU after treatment with sodium selenate in the hippocampus and amygdala compared to the vehicle ($H_2O$) treated controls can be seen.

References

Alonso, A. D. C. et al., Alzheimer's disease hyperphosphorylated tau sequesters normal tau into tangles of filaments and disassembles microtubules. Nat. Med., 1996. 2: p. 783-787.

Barrett, W. C., et al., Roles of superoxide radical anion in signal transduction mediated by reversible regulation of protein-tyrosine phosphatase 1B. J Biol Chem, 1999. 274 (49): p. 34543-6.

Barton, G. J., P. T. Cohen, and D. Barford, Conservation analysis and structure prediction of the protein serine/threonine phosphatases. Sequence similarity with diadenosine tetraphosphatase from Escherichia coli suggests homology to the protein phosphatases. Eur J Biochem, 1994. 220(1): p. 225-37.

Bass, D. A., et al., Flow cytometric studies of oxidative product formation by neutrophils: a graded response to membrane stimulation. J Immunol, 1983. 130(4): p. 1910-7.

Bramblett, G. T., et al., Abnormal tau phosphorylation at Ser396 in Alzheimer's disease recapitulates development and contributes to reduced microtubule binding. Neuron, 1993. 10: p.1089-1099.

Bryant, J. C., R. S. Westphal, and B. E. Wadzinski, Methylated C-terminal leucine residue of PP2A catalytic subunit is important for binding of regulatory Balpha subunit. Biochem J, 1999. 339 (Pt 2): p. 241-6.

Cayla, X., et al., Molecular cloning, expression, and characterization of PTPA, a protein that activates the tyrosyl phosphatase activity of protein phosphatase 2A. J Biol Chem, 1994. 269(22): p. 15668-75.

Chen, J., B. L. Martin, and D. L. Brautigan, Regulation of protein serine-threonine phosphatase type-2A by tyrosine-phosphorylation. Science, 1992. 257(5074): p. 1261-4.

Chen, J., S. Parsons, and D. L. Brautigan, Tyrosine phosphorylation of protein phosphatase 2A in response to growth stimulation and v-src transformation of fibroblasts. J Biol Chem, 1994. 269(11): p. 7957-62.

Cohen, P. T., Novel protein serine/threonine phosphatases: variety is the spice of life. Trends Biochem Sci, 1997. 22(7): p. 245-51.

Conway, K., Harper, J., Lansbury, P., 1998. Accelerated in vitro fibril formation by a mutant alpha-synuclein linked to early-onset Parkinson disease. Nat. Med. 4, 1318-1320.

Cross, D. A. et al., Inhibition of glycogen synthase kinase-3 by insulin mediated protein kinase B. Nature, 1995. 378 (6559): p. 785-9.

Diehl, J. A. et al., Glycogen synthase kinase-3 beta regulates cyclin DI proteolysis and cellular localization. Genes Dev., 1998. 12(22): p. 3499-511.

Duda, J. E., Giasson, B. I., Mabon, M. E., Miller, D. C., Golbe, L. I., Lee, V. M., Trojanowski, J. Q., 2002. Concurrence of alpha-synuclein and tau brain pathology in the Contursi kindred. Acta Neuropathol. (Berl.) 104, 7-11.

Ellman, G. L., A colorimetric method for determining low concentrations of mercaptans. Arch Biochem Biophys, 1958. 74(2): p. 443-50.

Feany, M. B., Bender, W. W., 2000. A *Drosophila* model of Parkinson's disease. Nature 404, 394-398.

Fernandez, J. J., et al., Okadaic acid, useful tool for studying cellular processes. Curr Med Chem, 2002. 9(2): p. 229-62.

Forman, M. S., Schmidt, M. L., Kasturi, S., Perl, D. P., Lee, V. M., Trojanowski, J.Q., 2002. Tau and alpha-synuclein pathology in amygdala of Parkinsonism-dementia complex patients of Guam. Am. J. Pathol. 160, 1725-1731.

Frasier, M. et al./Experimental Neurology 192 (2005) 274-287 285.

Gallego, M. and Virshup, D. M., 2005. Protein serine/threonine phosphatases: life, death, and sleeping. Curr Opin Cell Biol, 17(2):197-202.

Giasson, B. I., Duda, J. E., Quinn, S. M., Zhang, B., Trojanowski, J. Q., Lee, V. M., 2002. Neuronal alpha-synucleinopathy with severe movement disorder in mice expressing A53T human alpha-synuclein. Neuron 34, 521-533.

Giasson, B. I., Forman, M. S., Higuchi, M., Golbe, L. I., Graves, C. L., Kotzbauer, P. T., Trojanowski, J. Q., Lee, V. M., 2003. Initiation and synergistic fibrillization of tau and alpha-synuclein. Science 300, 636-640.

Grundke-Iqbal, I. et al., Microtubule-associated protein tau. A component of Alzheimer paired helical filaments. J. Biol. Chem. 1986a. 261: p. 6084-6089.

Grundke-Iqbal, I. et al., Abnormal phosphorylation of the microtubule-associated protein τ (tau) in Alzheimer cytoskeletal pathology. Proc. Natl. Acad. Sci. U.S.A. 1986b. 83: p4913-4917.

Guo, H. and Z. Damuni, Autophosphoiylation-activated protein kinase phosphorylates and inactivates protein phosphatase 2A. Proc Natl Acad Sci U S A, 1993. 90(6): p. 2500-4.

Hashimoto, M., L J, H., Xia, Y., Takeda, A., Sisk, A., Sundsmo, M., Masliah, E., 1999. Oxidative stress induces amyloid-like aggregate formation of NACP/a-synuclein in vitro. NeuroReport 10, 717-721.

He, X. et al., Glycogen synthase kinase-3 and dorsoventral patternin in Xenopus embryos. Nature, 1995, 374(6523): p. 617-22.

Ishizawa, T., Mattila, P., Davies, P., Wang, D., Dickson, D. W., 2003. Colocalization of tau and alpha-synuclein epitopes in Lewy bodies. J. Neuropathol. Exp. Neurol. 62, 389-397.

Jensen, P. H., Hager, H., Nielsen, M. S., Hojrup, P., Gliemann, J., Jakes, R., 1999. alpha-Synuclein binds to tau and stimulates the protein kinase Acatalyzed tau phosphorylation of serine residues 262 and 356. J. Biol. Chem. 274, 25481-25489.

Kahle, P. J., Neumann, M., Ozmen, L., Muller, V., Odoy, S., Okamoto, N., Jacobsen, H., Iwatsubo, T., Trojanowski, J. Q., Takahashi, H., Wakabayashi, K., Bogdanovic, N., Riederer, P., Kretzschmar, H. A., Haass, C., 2001. Selective insolubility of alpha-synuclein in human Lewy body diseases is recapitulated in a transgenic mouse model. Am. J. Pathol. 159, 2215-2225.

Kamibayashi, C. et al., Comparison of heterotrimeric protein phosphatases 2A containing different B subunits. J. Biol. Chem. 1994. 269: p.20139-20148.

Kohn, A. D., F. Takeuchi, and R. A. Roth, Akt, a pleckstrin homology domain containing kinase, is activated primarily by phosphorylation. J Biol Chem, 1996. 271(36): p. 21920-6.

Kruger, R., Kuhn, W., Muller, T., Woitalla, D., Graeber, M., Kosel, S., Przuntek, H., Epplen, J., Schols, L., Riess, O., 1998. Ala30Pro mutation in the gene encoding a-synuclein in Parkinson's disease. Nat. Genet. 18, 106-108.

Kwon, J., et al., Reversible oxidation and inactivation of the tumor suppressor PTEN in cells stimulated with peptide growth factors. Proc Natl Acad Sci U S A, 2004. 101(47): p. 16419-24.

Lee, J., et al., A specific protein carboxyl methylesterase that demethylates phosphoprotein phosphatase 2A in bovine brain. Proc. Natl. Acad. Sci. U.S.A., 1996. 93(12): p. 6043-7.

Lee, V. M- Y. et al., Neurodegenerative Taupathies. Annu. Rev. Neurosci. 2001. 24: p. 1121-1159.

Lee, V. M- Y. et al., A68: A major subunit of paired helical filaments and derivatized forms of normal tau. Science, 1991.251: p.675-678.

Li, T. and Paudel, H. K., Glycogen Synthase Kinase 3β phosphorylates Alzheimer's disease-specific Ser 396 of microtubule-associated protein tau by a sequential mechanism. Biochemistry, 2006, 45(10): p.3125-3133.

Liu, F., et al., Contributions of protein phophatases PP1, PP2A, PP2B and PP5 to the regulation of tau phosphorylation. Eur. J. Neurosci. 2005. 22(8): p. 1942-50.

Longin, S., et al., An inactive protein phosphatase 2A population is associated with methylesterase and can be reactivated by the phosphotyrosyl phosphatase activator. Biochem J, 2004. 380(Pt 1): p. 111-9.

Masliah, E., Rockenstein, E., Veinbergs, I., Mallory, M., Hashimoto, M., Takeda, A., Sagara, Y., Sisk, A., Mucke, L., 2000. Dopaminergic loss and inclusion body formation in alpha-synuclein mice: inplications for neurodegenerative disorders. Science 287, 1265-1269.

Mumby, M. C. and Walter, G., Protein serine/threonine phosphatases: structure, regulation and functions in cell growth. Physiol. Rev. 1993. 73: p. 673-700.

Ostrerova-Golts, N., Petrucelli, L., Hardy, J., Lee, J., Farrer, M., Wolozin, B., 2000. The A53T a-synuclein mutation increases iron-dependent aggregation and toxicity. J. Neurosci. 20, 6048-6054.

Paik, S., Shin, H., Lee, J., Chang, C., Kim, J., 1999. Copper (II)-induced self-oligomerization of a-synuclein. Biochem. J. 340, 821-828.

Paik, S. R., Shin, H. J., Lee, J. H., 2000. Metal-catalyzed oxidation of alphasynuclein in the presence of copper(II) and hydrogen peroxide. Arch. Biochem. Biophys. 378, 269-277.

Peterson, R. T., et al., 1999. Protein phosphatase 2A interacts with the 70-kDa S6 kinase and is activated by inhibition of FKBP12-rapamycinassociated protein. Proc Natl Acad Sci USA, 96(8):4438-42.

Polymeropoulos, M. H., Lavedan, C., Leroy, E., Ide, S. E., Dehejia, A., Dutra, A., Pike, B., Root, H., Rubenstein, J., Boyer, R., Stenroos, E. S., Chandrasekharappa, S., Athanassiadou, A., Papapetropoulos, T., Johnson, W. G., Lazzarini, A. M., Duvoisin, R. C., Di Iorio, G., Golbe, L. I., Nussbaum, R. L., 1997. Mutation in the alpha-synuclein gene identified in families with Parkinson's disease. Science 276, 2045-2047.

Salmeen, A., et al., Redox regulation of protein tyrosine phosphatase 1B involves a sulphenyl-amide intermediate. Nature, 2003. 423(6941): p. 769-73.

Silverstein, A. M., et al., 2002. Ations of PP2A on the MAP kinase pathway and apoptosis are mediated by distinct regulatory subunits. Proc Natl Acad Sci USA, 99(7):4221-6.

Singleton, A. B., Farrer, M., Johnson, J., Singleton, A., Hague, S., Kachergus, J., Hulihan, M., Peuralinna, T., Dutra, A., Nussbaum, R., Lincoln, S., Crawley, A., Hanson, M., Maraganore, D., Adler, C., Cookson, M. R., Muenter, M., Baptista, M., Miller, D., Blancato, J., Hardy, J., Gwinn-Hardy, K., 2003. alpha-Synuclein locus triplication causes Parkinson's disease. Science 302, 841.

Sohn, J. and J. Rudolph, Catalytic and chemical competence of regulation of cdc25 phosphatase by oxidation/reduction. Biochemistry, 2003. 42(34): p. 10060-70.

Sontag, E. et al., A novel pool of protein phosphatase 2A is associated with microtubules and is regulated during the cell cycle. J. Cell Biol., 1995. 128: p. 1131-1144.

Sontag, E. et al., Regulation of the phosphorylation state and microtubule-binding activity of Tau by protein phosphatase 2A. Neuron, 1996. 17: p. 1201-1207.

Spillantini, M., Schmidt, M., V M -Y, L., Trojanowski, J., Jakes, R., Goedert, M., 1997. a-Synuclein in Lewy bodies. Nature 388, 839-840.

Spillantini, M. G., Crowther, R. A., Jakes, R., Hasegawa, M., Goedert, M., 1998b. a-Synuclein in filamentous inclusions of Lewy bodies from Parkinson's disease and dementia with Lewy bodies. Proc. Natl. Acad. Sci. U.S.A. 95, 6469-6473.

Tolstykh, T., et al., Carboxyl methylation regulates phosphoprotein phosphatase 2A by controlling the association of regulatory B subunits. Embo J, 2000.19(21): p.5682-91.

Van Hoof, C., et al., Specific interactions of PP2A and PP2A-like phosphatases with the yeast PTPA homologues, Ypa1 and Ypa2. Biochem J, 2005. 386(Pt 1): p. 93-102.

Van Kanegan, M. J., et al., 2005. Distinct protein phosphatase 2A heterotrimers modulate growth factor signalling to extracellular signal-regulated kinases and Akt. J Biol Chem, 280(43):36029-36.

Wang, J. Z., et al., Dephosphorylation of Alzheimer paired helical filaments by protein phosphatase 2A and 2B. J. Biol. Chem. 1995. 270: p. 4854-4860.

Wang, J. Z., et al., Restoration of biological activity of Alzheimer abnormally phosphorylated tau by dephosphorylation with protein phosphatase 2A, 2B and 1. Mol. Brain Res. 1996. 38: p. 200-208.

Wang, X., V. C. Culotta, and C. B. Klee, Superoxide dismutase protects calcineurin from inactivation. Nature, 1996. 383(6599): p. 434-7.

Welsh, G. I. et al., T-cell activation leads to rapid stimulation of translation initiation factor eIF2B and inactivation of glycogen synthase kinase-3. J. Biol. Chem. 1996. 271(19): p. 11410-3.

Wera, S. and B. A. Hemmings, Serine/threonine protein phosphatases. Biochem J, 1995. 311 (Pt 1): p. 17-29.

Woetmann, A., et al., 2003. Protein phosphatase 2A (PP2A) regulates interleukin-4-mediated STAT6 signaling. J Biol Chem, 278(5):2787-91.

Wu, J., et al., Carboxyl methylation of the phosphoprotein phosphatase 2A catalytic subunit promotes its functional association with regulatory subunits in vivo. Embo J, 2000. 19(21): p. 5672-81.

Xie, H. and S. Clarke, Protein phosphatase 2A is reversibly modified by methyl esterification at its C-terminal leucine residue in bovine brain. J Biol Chem, 1994. 269(3): p. 1981-4.

Zarranz, J. J., Alegre, J., Gomez-Esteban, J. C., Lezcano, E., Ros, R., Ampuero, I., Vidal, L., Hoenicka, J., Rodriguez, O., Atares, B., Llorens, V., Tortosa, E. G., Del Ser, T., Munoz, D. G., DeYebenes, J. G., 2004. The new mutation, E46K, of alpha-synuclein causes Parkinson and Lewy body dementia. Ann. Neurol. 55, 164-173.

Zhu, D., et al., 2004. Galpha12 directly interacts with PP2A: evidence FOR Galpha12-stimulated PP2A phosphatase activity and dephosphorylation of microtubule-associated protein, tau. J Biol Chem, 279(53):54983-6.

The invention claimed is:

1. A method for the treatment of a tauopathy selected from Pick's disease and primary progressive aphasia in a subject in need thereof, said method comprising administering to the subject an effective amount of selenate or a pharmaceutically acceptable salt thereof, with the proviso that the pharmaceutically acceptable salt of selenate is not lithium selenate and wherein the selenate or pharmaceutically acceptable salt thereof is administered in an amount that provides 0.07 mg/kg to 6.5 mg/kg of selenium to the subject per day.

2. The method according to claim 1 further comprising the administration of another therapy for treatment of a tauopathy selected from Pick's disease and primary progressive aphasia, or a therapy for relieving the symptoms of a tauopathy selected from Pick's disease and primary progressive aphasia.

3. A method for the treatment of a tauopathy selected from Pick's disease and primary progressive aphasia, in a subject in need thereof, said method comprising administering to the subject an effective amount of selenate or a pharmaceutically acceptable salt thereof, with the proviso that the pharmaceutically acceptable salt of selenate is not lithium selenate and wherein the selenate or pharmaceutically acceptable salt thereof is administered to the subject in an amount that provides 0.07 mg/kg to 6.5 mg/kg per day of selenate.

4. A method for the treatment of a tauopathy selected from Pick's disease and primary progressive aphasia, in a subject in need thereof, said method comprising administering to the subject an effective amount of selenate or a pharmaceutically acceptable salt thereof, with the proviso that the pharmaceutically acceptable salt of selenate is not lithium selenate and wherein the selenate or pharmaceutically acceptable salt thereof is sodium selenate and the sodium selenate is administered in an amount of 0.07 mg/kg to 6.5 mg/kg per day.

5. A method for the treatment of a tauopathy selected from Pick's disease and primary progressive aphasia, in a subject in need thereof, said method comprising administering to the subject an effective amount of selenate or a pharmaceutically acceptable salt thereof, wherein the selenate or pharmaceutically acceptable salt thereof is selected from sodium selenate, potassium selenate, calcium selenate, magnesium selenate, iron selenate, nickel selenate, zinc selenate, ammonium selenate and alkylammonium selenate and the sodium selenate, potassium selenate, calcium selenate, magnesium selenate, iron selenate, nickel selenate, zinc selenate, ammonium selenate and alkylammonium selenate is administered in an amount of 0.1 to 14 mg/kg per day.

6. The method according to claim 3 further comprising the administration of another therapy for treatment of a tauopathy selected from Pick's disease and primary progressive aphasia, or a therapy for relieving the symptoms of a tauopathy selected from Pick's disease and primary progressive aphasia.

7. The method according to claim 4 further comprising the administration of another therapy for treatment of a tauopathy selected from Pick's disease and primary progressive aphasia, or a therapy for relieving the symptoms of a tauopathy selected from Pick's disease and primary progressive aphasia.

8. The method according to claim 5 further comprising the administration of another therapy for treatment of a tauopathy selected from Pick's disease and primary progressive aphasia, or a therapy for relieving the symptoms of a tauopathy selected from Pick's disease and primary progressive aphasia.

9. A method for the treatment of a tauopathy selected from Pick's disease and primary progressive aphasia, in a subject in need thereof, said method comprising administering to the subject an effective amount of selenate or a pharmaceutically acceptable salt thereof, wherein the selenate or pharmaceutically acceptable salt thereof is not administered with another therapy.

* * * * *